(12) United States Patent
Han et al.

(10) Patent No.: US 10,539,546 B2
(45) Date of Patent: Jan. 21, 2020

(54) MEASURING PHOSPHORUS IN WASTEWATER USING A SELF-ORGANIZING RBF NEURAL NETWORK

(71) Applicant: Beijing University of Technology, Beijing (CN)

(72) Inventors: Honggui Han, Beijing (CN); Junfei Qiao, Beijing (CN); Wendong Zhou, Beijing (CN)

(73) Assignee: Zhengbiao Ouyang, Shenzhen (CN)

( * ) Notice: Subject to any disclaimer, the term of this patent is extended or adjusted under 35 U.S.C. 154(b) by 0 days.

(21) Appl. No.: 15/891,175

(22) Filed: Feb. 7, 2018

(65) Prior Publication Data

US 2018/0164272 A1 Jun. 14, 2018

Related U.S. Application Data

(63) Continuation-in-part of application No. 14/620,088, filed on Nov. 2, 2015.

(30) Foreign Application Priority Data

Nov. 2, 2014 (CN) .......................... 2014 1 0602859

(51) Int. Cl.
*G01N 31/00* (2006.01)
*G01N 33/18* (2006.01)
(Continued)

(52) U.S. Cl.
CPC ............. *G01N 33/18* (2013.01); *C02F 3/006* (2013.01); *C02F 3/30* (2013.01); *G06N 3/006* (2013.01);
(Continued)

(58) Field of Classification Search
CPC ...... G01N 33/18; G01N 33/188; G06N 3/088; G06N 3/0445; G06N 3/006; G06N 3/08;
(Continued)

(56) References Cited

U.S. PATENT DOCUMENTS

| 8,216,517 B2 * | 7/2012 | Prasad | ................. G05B 13/048 210/614 |
| 8,252,182 B1 * | 8/2012 | Chang | ..................... B01J 20/10 210/170.08 |

(Continued)

*Primary Examiner* — Robert G Bachner
(74) *Attorney, Agent, or Firm* — Zhihua Han

(57) ABSTRACT

In various implementations, methods and systems are designed for predicting effluent total phosphorus (TP) concentrations in an urban wastewater treatment process (WWTP). To improve the efficiency of TP prediction, a particle swarm optimization self-organizing radial basis function (PSO-SORBF) neural network may be established. Implementations may adjust structures and parameters associated with the neural network to train the neural network. The implementations may predict the effluent TP concentrations with reasonable accuracy and allow timely measurement of the effluent TP concentrations. The implementations may further collect online information related to the estimated effluent TP concentrations. This may improve the quality of monitoring processes and enhance management of WWTP.

14 Claims, 19 Drawing Sheets

(51) Int. Cl.
*G06N 3/08* (2006.01)
*C02F 3/30* (2006.01)
*C02F 3/00* (2006.01)
*G06N 3/00* (2006.01)
*G06N 3/04* (2006.01)
*C02F 101/10* (2006.01)

(52) U.S. Cl.
CPC ......... *G06N 3/0472* (2013.01); *G06N 3/0481* (2013.01); *G06N 3/08* (2013.01); *G06N 3/088* (2013.01); *C02F 3/308* (2013.01); *C02F 2101/105* (2013.01); *C02F 2209/001* (2013.01); *C02F 2209/003* (2013.01); *C02F 2209/005* (2013.01); *C02F 2209/02* (2013.01); *C02F 2209/04* (2013.01); *C02F 2209/06* (2013.01); *C02F 2209/08* (2013.01); *C02F 2209/10* (2013.01); *C02F 2209/16* (2013.01); *C02F 2209/22* (2013.01)

(58) Field of Classification Search
CPC . B25J 5/007; C02F 2101/16; C02F 2209/001; C02F 2209/006; C02F 2209/04; C02F 2209/10; C02F 2209/14; C02F 2209/18; C02F 2209/22; C02F 2209/40; C02F 3/006; G05B 19/406; G05B 2219/40585
See application file for complete search history.

(56) References Cited

U.S. PATENT DOCUMENTS

| | | | |
|---|---|---|---|
| 2015/0053612 A1* | 2/2015 | Bitan-Banin | C02F 3/006 210/613 |
| 2016/0140437 A1* | 5/2016 | Qiao | G01N 33/18 706/21 |

* cited by examiner

Table 1. The training samples of influent TP (mg/L)

| | | | | | | | | | |
|---|---|---|---|---|---|---|---|---|---|
| 3.9021 | 3.8943 | 4.3182 | 4.2219 | 4.6025 | 4.3496 | 4.5057 | 4.5057 | 4.5057 | 4.5057 |
| 3.8848 | 3.8155 | 3.9287 | 4.0154 | 4.1802 | 4.1465 | 4.1465 | 4.1465 | 4.1465 | 4.1465 |
| 4.1465 | 4.1465 | 4.2845 | 3.8326 | 3.7941 | 4.4504 | 4.3140 | 4.4706 | 4.2410 | 4.5929 |
| 4.4944 | 3.8420 | 3.8664 | 4.0551 | 4.2081 | 4.1305 | 4.2712 | 3.5370 | 2.8337 | 4.1774 |
| 3.7040 | 3.6206 | 4.1277 | 4.0534 | 4.3345 | 4.1899 | 4.3530 | 4.2267 | 4.1365 | 4.0805 |
| 4.0221 | 3.9322 | 3.8749 | 4.0820 | 4.0727 | 4.1665 | 4.2180 | 4.1436 | 4.3808 | 4.4049 |
| 4.2351 | 4.2345 | 4.1325 | 3.9768 | 3.9608 | 3.7857 | 3.8670 | 3.8294 | 3.9176 | 4.0762 |
| 4.0099 | 4.1032 | 4.0226 | 4.0941 | 4.1105 | 4.1284 | 4.0332 | 4.0053 | 3.9005 | 3.8975 |
| 3.7953 | 3.8648 | 3.8835 | 3.9725 | 4.2412 | 4.4562 | 4.2018 | 4.1647 | 4.5131 | 4.1541 |
| 4.0418 | 4.0789 | 3.9439 | 3.7140 | 3.9232 | 4.0274 | 3.9716 | 4.0438 | 4.2394 | 4.2394 |
| 4.2394 | 4.2394 | 4.2394 | 4.2394 | 4.2394 | 4.2394 | 4.2394 | 4.2392 | 4.2392 | 4.2392 |
| 4.2392 | 4.2392 | 4.2392 | 4.2392 | 3.6244 | 4.2873 | 4.0612 | 3.9821 | 4.0342 | 4.0920 |
| 4.0371 | 4.0575 | 4.1273 | 4.1907 | 4.2153 | 4.2907 | 4.1859 | 4.1446 | 4.0744 | 4.3648 |
| 3.8792 | 3.7862 | 3.8169 | 3.7380 | 3.8215 | 4.0155 | 4.0076 | 3.9549 | 4.0678 | 4.0160 |
| 3.9320 | 4.0386 | 3.9331 | 3.8880 | 3.7802 | 3.6751 | 3.6112 | 3.6098 | 3.6671 | 3.6269 |
| 3.7581 | 3.8980 | 4.0578 | 3.9783 | 3.9331 | 3.9794 | 4.0795 | 4.1422 | 4.7669 | 4.3334 |
| 4.4615 | 4.1052 | 4.0354 | 4.0672 | 4.2935 | | | | | |

Figure. 7

Table 2. The training samples of temperature (°C)

| | | | | | | | | | |
|---|---|---|---|---|---|---|---|---|---|
| 27.2087 | 27.2933 | 27.3170 | 27.3022 | 27.2354 | 27.1584 | 27.0976 | 26.9526 | 26.8788 | 26.6723 |
| 26.8153 | 26.9290 | 27.1494 | 27.2028 | 27.2147 | 27.1909 | 27.1732 | 27.1331 | 27.1094 | 27.0000 |
| 26.9556 | 26.8655 | 26.8153 | 26.7652 | 26.8138 | 26.5134 | 26.3578 | 26.1585 | 26.0751 | 26.0444 |
| 26.0429 | 25.9539 | 26.0210 | 26.0064 | 25.9363 | 25.9086 | 25.8211 | 25.6522 | 25.5824 | 25.3617 |
| 24.9826 | 24.9667 | 24.7476 | 25.0649 | 25.2646 | 25.0490 | 24.9292 | 24.8931 | 24.8657 | 24.8729 |
| 24.9177 | 24.9566 | 24.9725 | 24.9595 | 24.9307 | 24.9047 | 24.8859 | 24.8686 | 24.8225 | 24.7908 |
| 24.7231 | 24.7015 | 24.6439 | 24.6353 | 24.6655 | 24.9018 | 24.9768 | 25.1488 | 25.1560 | 25.1589 |
| 25.1488 | 25.1097 | 25.0852 | 25.0331 | 24.9840 | 24.9119 | 24.8614 | 24.7649 | 24.7130 | 24.5476 |
| 24.4801 | 24.4600 | 24.4384 | 24.4198 | 24.3337 | 24.2878 | 24.2191 | 24.1833 | 24.0703 | 24.0088 |
| 23.8717 | 23.8018 | 23.6935 | 23.7533 | 23.9902 | 24.1218 | 24.2721 | 24.2950 | 24.3194 | 24.3022 |
| 24.2620 | 24.2291 | 24.1546 | 24.0245 | 23.8745 | 23.7790 | 23.7806 | 24.1907 | 24.1592 | 23.9890 |
| 23.9090 | 23.7450 | 23.6837 | 23.6367 | 23.6253 | 23.6295 | 23.6239 | 23.6310 | 23.6253 | 23.6082 |
| 23.5968 | 23.5470 | 23.5114 | 23.4318 | 23.3835 | 23.2770 | 23.2146 | 23.0870 | 23.0403 | 22.9625 |
| 22.9851 | 23.0559 | 23.0743 | 23.1877 | 23.2032 | 23.1834 | 23.1707 | 23.1409 | 23.0956 | 23.0630 |
| 23.0134 | 22.9115 | 22.8593 | 22.7420 | 22.7448 | 22.8084 | 22.9144 | 23.1381 | 23.2841 | 23.5598 |
| 23.6338 | 23.6751 | 23.7307 | 23.7535 | 23.7378 | 23.6295 | 23.5570 | 23.4958 | 23.4048 | 23.4006 |
| 23.4048 | 23.4190 | 23.8191 | 23.8477 | 23.8905 | | | | | |

Figure. 8

Table 3. The training samples of ORP in anaerobic terminal

| | | | | | | | | |
|---|---|---|---|---|---|---|---|---|
| 540.2970 | 546.8350 | 554.3970 | 556.1280 | 553.4360 | 551.0650 | 549.9110 | 554.5260 | 556.3200 | 561.1910 |
| 555.0380 | 548.5010 | 550.9370 | 563.9470 | 564.7160 | 565.2290 | 565.2290 | 565.1010 | 563.7550 | 564.7160 |
| 564.7800 | 565.6140 | 565.6140 | 564.6520 | 563.8830 | 566.1260 | 565.5500 | 565.2290 | 564.8440 | 470.6930 |
| 480.6910 | 414.3560 | 539.2080 | 555.3590 | 557.9870 | 558.8200 | 558.9480 | 526.9660 | 470.4370 | 567.4720 |
| 565.1650 | 563.8190 | 578.6880 | 581.2520 | 581.2520 | 582.1490 | 581.8290 | 581.7650 | 581.7650 | 581.2520 |
| 580.9960 | 580.4830 | 579.8420 | 579.7140 | 579.7780 | 580.4190 | 580.7390 | 580.5470 | 580.7390 | 580.4830 |
| 580.0980 | 580.0340 | 579.0730 | 578.6240 | 578.2400 | 578.3040 | 576.9580 | 577.4070 | 577.9830 | 578.2400 |
| 578.1760 | 577.8550 | 577.7270 | 577.4710 | 577.2780 | 577.0860 | 576.8940 | 576.8940 | 577.4070 | 575.0350 |
| 572.9840 | 573.7530 | 574.9070 | 574.7790 | 575.0990 | 575.2270 | 573.8170 | 572.2150 | 572.6640 | 573.0480 |
| 572.4070 | 572.0230 | 571.4460 | 573.9460 | 573.8170 | 573.9460 | 574.2660 | 574.9070 | 575.7400 | 575.7400 |
| 575.0990 | 575.0350 | 574.5860 | 574.1380 | 573.9460 | 573.6890 | 573.3050 | 575.0350 | 574.8430 | 574.1380 |
| 574.0100 | 573.6890 | 573.7530 | 572.0230 | 570.9970 | 570.1000 | 569.9720 | 570.7410 | 571.7020 | 572.1510 |
| 572.1510 | 572.6640 | 573.2410 | 573.3690 | 573.1760 | 573.1120 | 573.0480 | 573.0480 | 573.1120 | 573.1760 |
| 574.5860 | 578.3680 | 578.7530 | 577.2780 | 573.2410 | 570.4210 | 570.9330 | 572.0870 | 572.1510 | 570.2920 |
| 570.0360 | 568.7540 | 567.0240 | 568.4340 | 569.0100 | 568.8820 | 568.9460 | 569.2670 | 569.4590 | 569.5230 |
| 570.1000 | 571.5100 | 572.4070 | 572.8560 | 572.1510 | 570.6770 | 570.3560 | 569.9720 | 569.6510 | 569.5870 |
| 569.7150 | 570.1640 | 570.8690 | 570.9330 | 571.5740 | | | | | |

Figure. 9

Table 4. The training samples of DO in front of aerobic (mg/L)

| | | | | | | | | |
|---|---|---|---|---|---|---|---|---|
| 0.0518 | 0.0394 | 0.0379 | 0.0356 | 0.0370 | 0.0361 | 0.0467 | 0.0417 | 0.0510 | 0.0382 |
| 0.0411 | 0.0363 | 0.0472 | 0.0581 | 0.0514 | 0.0561 | 0.0673 | 0.0585 | 0.0507 | 0.0486 |
| 0.0484 | 0.0492 | 0.1343 | 0.0793 | 0.0561 | 0.0696 | 0.0427 | 0.0441 | 0.0480 | 0.0571 |
| 0.0464 | 0.0425 | 0.0540 | 0.0711 | 0.0715 | 0.0535 | 0.0792 | 0.0603 | 0.0522 | 0.0375 |
| 0.0391 | 0.0382 | 0.0318 | 0.0339 | 0.0312 | 0.0831 | 0.0403 | 0.0353 | 0.0411 | 0.0355 |
| 0.0501 | 0.0384 | 0.0371 | 0.0962 | 0.0497 | 0.0666 | 0.0398 | 0.0427 | 0.0663 | 0.0416 |
| 0.0640 | 0.0555 | 0.0796 | 0.0768 | 0.0615 | 0.0592 | 0.0946 | 0.0530 | 0.0769 | 0.0450 |
| 0.0823 | 0.0397 | 0.0567 | 0.0390 | 0.0396 | 0.0716 | 0.0423 | 0.0637 | 0.0448 | 0.3747 |
| 0.3764 | 0.4340 | 0.4833 | 0.4329 | 0.4512 | 0.4455 | 0.5192 | 0.4821 | 0.4478 | 0.4694 |
| 0.4844 | 0.5815 | 0.5309 | 0.9670 | 0.8274 | 0.7756 | 0.4701 | 0.4711 | 0.4316 | 0.4357 |
| 0.4621 | 0.4867 | 0.5287 | 0.5043 | 0.5440 | 0.5487 | 0.5110 | 0.4867 | 0.4889 | 0.5043 |
| 0.5378 | 0.5487 | 0.5400 | 1.5057 | 1.0497 | 0.9117 | 0.9334 | 0.8063 | 0.4684 | 0.4649 |
| 0.4508 | 0.3812 | 0.3495 | 0.3594 | 0.3574 | 0.3821 | 0.3640 | 0.3554 | 0.3703 | 1.0503 |
| 0.7617 | 0.5861 | 0.5539 | 0.4448 | 0.2693 | 0.2558 | 0.2740 | 0.3096 | 0.2734 | 0.2962 |
| 0.2997 | 0.3444 | 0.3165 | 0.2646 | 0.2404 | 0.3987 | 0.3624 | 0.3024 | 0.3268 | 0.2476 |
| 0.2465 | 0.2079 | 0.2103 | 0.2380 | 0.2519 | 0.2651 | 0.2470 | 0.2557 | 0.2890 | 0.2659 |
| 0.9111 | 0.7375 | 0.2701 | 0.2665 | 0.2489 | | | | | |

Figure. 10

Table 5. The training samples of TSS in aerobic terminal (mg/L)

| | | | | | | | | |
|---|---|---|---|---|---|---|---|---|
| 2.8251 | 2.7176 | 2.7700 | 2.8094 | 2.7666 | 2.7748 | 2.7823 | 2.7998 | 2.8015 | 2.7686 |
| 2.7556 | 2.7975 | 2.8011 | 2.8182 | 2.8985 | 2.8089 | 2.7813 | 2.8060 | 3.1727 | 2.9242 |
| 2.8536 | 2.8202 | 2.8179 | 2.9067 | 2.7963 | 2.8271 | 2.8168 | 2.8262 | 2.8678 | 2.8074 |
| 2.8428 | 2.8260 | 2.8615 | 2.7277 | 2.7863 | 2.8132 | 2.7385 | 2.8738 | 2.8651 | 2.9005 |
| 2.9324 | 2.8942 | 2.8223 | 2.8512 | 2.7712 | 2.6251 | 2.5540 | 2.4976 | 2.6220 | 2.6049 |
| 2.5314 | 2.5817 | 2.5765 | 2.5590 | 2.5611 | 2.5664 | 2.5177 | 2.4709 | 2.4971 | 2.4192 |
| 2.4831 | 2.5234 | 2.4654 | 2.4501 | 2.4564 | 2.4367 | 2.4777 | 2.4562 | 2.4776 | 2.4068 |
| 2.4583 | 2.4031 | 2.4443 | 2.5130 | 2.4505 | 2.4376 | 2.3933 | 2.4439 | 2.4637 | 2.4573 |
| 2.4982 | 2.5214 | 2.4515 | 2.3733 | 2.4492 | 2.4602 | 2.4725 | 2.4949 | 2.4815 | 2.5655 |
| 2.5286 | 2.4330 | 2.4429 | 2.4573 | 2.4820 | 2.6305 | 2.5025 | 2.4821 | 2.4912 | 2.4121 |
| 2.4265 | 2.4700 | 2.4481 | 2.4801 | 2.5045 | 2.4743 | 2.4331 | 2.4700 | 2.3919 | 2.4801 |
| 2.4472 | 2.4743 | 2.4740 | 2.5777 | 2.4818 | 2.5754 | 2.5450 | 2.5624 | 2.5353 | 2.4304 |
| 2.3899 | 2.3654 | 2.4347 | 2.3155 | 2.3089 | 2.2740 | 2.3947 | 2.2430 | 2.3166 | 2.2692 |
| 2.2784 | 2.3157 | 2.2768 | 2.1761 | 2.2200 | 2.1312 | 2.3333 | 2.4261 | 2.4155 | 2.3439 |
| 2.3083 | 2.3119 | 2.2717 | 2.2823 | 2.4388 | 2.4274 | 2.5251 | 2.4161 | 2.4789 | 2.3514 |
| 2.3938 | 2.2736 | 2.3839 | 2.3818 | 2.4428 | 2.4255 | 2.3938 | 2.4187 | 2.5133 | 2.4147 |
| 2.5321 | 2.4440 | 2.3300 | 2.2835 | 2.4055 | | | | | |

Figure. 11

Table 6. The training samples of effluent pH

| | | | | | | | | |
|---|---|---|---|---|---|---|---|---|
| 7.9266 | 7.9298 | 7.9266 | 7.9176 | 7.8907 | 7.8718 | 7.8641 | 7.8520 | 7.8465 | 7.8448 |
| 7.8536 | 7.8579 | 7.8643 | 7.8643 | 7.8655 | 7.8645 | 7.8623 | 7.8568 | 7.8581 | 7.8595 |
| 7.8619 | 7.8632 | 7.8690 | 7.8713 | 7.8801 | 7.9154 | 7.9079 | 7.9038 | 7.9029 | 7.9466 |
| 7.9524 | 7.8931 | 7.9049 | 7.9176 | 7.9166 | 7.9110 | 7.8953 | 7.8901 | 7.8949 | 8.0150 |
| 8.0054 | 8.0039 | 7.9967 | 8.0228 | 7.9988 | 7.9917 | 7.9863 | 7.9852 | 7.9898 | 7.9908 |
| 7.9962 | 7.9949 | 7.9981 | 8.0005 | 7.9996 | 8.0042 | 8.0112 | 8.0102 | 8.0000 | 7.9967 |
| 7.9946 | 7.9947 | 7.9856 | 7.9844 | 7.9933 | 7.9970 | 7.9909 | 8.0009 | 8.0056 | 8.0036 |
| 8.0003 | 7.9993 | 8.0028 | 8.0065 | 8.0043 | 8.0035 | 8.0025 | 8.0028 | 8.0041 | 8.0044 |
| 8.0137 | 8.0184 | 8.0276 | 8.0242 | 8.0302 | 8.0337 | 8.0225 | 8.0443 | 8.0150 | 8.0210 |
| 8.0272 | 8.0274 | 8.0278 | 8.0275 | 8.0334 | 8.0398 | 8.0430 | 8.0217 | 8.0403 | 8.0348 |
| 8.0261 | 8.0217 | 8.0151 | 8.0088 | 8.0128 | 8.0119 | 7.9982 | 8.0523 | 8.0184 | 8.0088 |
| 8.0091 | 8.0119 | 8.0132 | 7.9865 | 7.9966 | 8.0214 | 8.0305 | 8.0108 | 8.0649 | 8.0616 |
| 8.0617 | 8.0597 | 8.0542 | 8.0328 | 8.0260 | 8.0137 | 8.0140 | 8.0399 | 8.0097 | 8.0142 |
| 8.0106 | 8.0296 | 8.0339 | 8.0221 | 8.0095 | 8.0303 | 8.0385 | 8.0153 | 8.0412 | 8.0335 |
| 8.0279 | 8.0111 | 7.9768 | 8.0001 | 8.0139 | 8.0204 | 8.0164 | 8.0097 | 8.0182 | 8.0221 |
| 8.0277 | 8.0347 | 8.0314 | 8.0202 | 8.0157 | 8.0092 | 8.0107 | | 8.0146 | 8.0159 |
| 8.0146 | 8.0166 | 8.0448 | 8.0585 | 8.0826 | | | | | |

Figure. 12

Table 7. The training samples of real effluent TP (mg/L)

| | | | | | | | | | |
|---|---|---|---|---|---|---|---|---|---|
| 2.1840 | 2.5480 | 2.7260 | 3.0020 | 2.8280 | 3.1680 | 2.6980 | 3.1300 | 3.3240 | 2.8240 |
| 2.3180 | 2.6040 | 2.5300 | 2.7300 | 2.5420 | 2.6960 | 2.6480 | 2.6680 | 2.8320 | 2.9860 |
| 2.8300 | 2.7300 | 3.0540 | 2.7600 | 2.3800 | 2.7520 | 3.0320 | 3.0800 | 2.9740 | 2.8620 |
| 2.9040 | 2.6060 | 2.4160 | 2.5280 | 2.7260 | 2.7100 | 2.7320 | 2.5980 | 2.8060 | 2.3240 |
| 1.8160 | 1.7320 | 1.5180 | 1.4300 | 1.4420 | 0.2620 | 0.2300 | 0.2380 | 0.2430 | 0.2240 |
| 0.2040 | 0.1860 | 0.1860 | 0.1820 | 0.1960 | 0.1900 | 0.1820 | 0.1800 | 0.1780 | 0.1760 |
| 0.1760 | 0.1800 | 0.1920 | 0.2200 | 0.4940 | 0.6720 | 0.6720 | 0.1980 | 0.1700 | 0.1740 |
| 0.1800 | 0.1700 | 0.1740 | 0.1780 | 0.1800 | 0.1820 | 0.1940 | 0.1940 | 0.1880 | 0.1880 |
| 0.1860 | 0.1840 | 0.1780 | 0.1620 | 0.1660 | 0.1760 | 0.1820 | 0.1820 | 0.2440 | 0.2420 |
| 0.2340 | 0.2220 | 0.2180 | 0.1780 | 0.1660 | 0.1660 | 0.1520 | 0.1520 | 0.1500 | 0.1500 |
| 0.1460 | 0.1520 | 0.1500 | 0.1540 | 0.1520 | 0.1680 | 0.3660 | 0.1520 | 0.1520 | 0.1540 |
| 0.1700 | 0.1680 | 0.1720 | 0.4540 | 0.5620 | 0.2900 | 0.2200 | 0.1960 | 0.1900 | 0.1720 |
| 0.1740 | 0.1740 | 0.1600 | 0.1660 | 0.1980 | 0.2100 | 0.1900 | 0.2160 | 0.2300 | 0.2140 |
| 0.2520 | 0.2680 | 0.2760 | 0.2620 | 0.2800 | 0.2620 | 0.2600 | 0.2760 | 0.1840 | 0.1620 |
| 0.1520 | 0.1760 | 0.2800 | 0.2340 | 0.2180 | 0.1920 | 0.1800 | 0.1540 | 0.1720 | 0.1600 |
| 0.1360 | 0.1520 | 0.1500 | 0.1480 | 0.1460 | 0.1600 | 0.1820 | 0.1940 | 0.1800 | 0.1860 |
| 0.1960 | 0.2040 | 0.1820 | 0.1740 | 0.1800 | | | | | |

Figure. 13

Table 8. The outputs of PSO-SORBF neural network in the training process

| | | | | | | | | | |
|---|---|---|---|---|---|---|---|---|---|
| 2.5924 | 2.5774 | 2.7139 | 2.7420 | 2.9675 | 3.0239 | 3.0842 | 3.1230 | 3.1272 | 3.0868 |
| 2.8836 | 2.8667 | 2.9053 | 2.9197 | 2.9894 | 2.9650 | 2.9599 | 2.9976 | 3.0031 | 2.9737 |
| 2.9440 | 2.9089 | 2.8114 | 2.7042 | 2.6578 | 2.5369 | 2.5271 | 2.5353 | 2.4798 | 2.4630 |
| 2.4328 | 2.6281 | 2.4591 | 2.2709 | 2.3057 | 2.3456 | 2.4002 | 2.3915 | 2.1636 | 1.6237 |
| 1.5660 | 1.5352 | 1.0574 | 1.1513 | 1.1869 | 0.4959 | 0.4875 | 0.2764 | 0.4341 | 0.4046 |
| 0.2318 | 0.4215 | 0.4384 | 0.2871 | 0.3424 | 0.2995 | 0.2495 | 0.1397 | 0.3020 | 0.3084 |
| 0.1314 | 0.1960 | 0.0802 | 0.0858 | 0.1052 | 0.3151 | 0.3704 | 0.4992 | 0.4119 | 0.3990 |
| 0.3661 | 0.4018 | 0.3592 | 0.4316 | 0.3456 | 0.2509 | 0.2479 | 0.1714 | 0.1937 | -0.0293 |
| 0.1276 | 0.1028 | 0.0249 | -0.0646 | 0.0254 | 0.2454 | 0.0718 | 0.1151 | 0.3470 | 0.1318 |
| 0.0875 | 0.1117 | 0.0899 | 0.5474 | 0.4004 | 0.5218 | 0.0957 | 0.0653 | 0.0755 | -0.0135 |
| -0.0145 | 0.0152 | 0.0313 | 0.0330 | 0.1000 | 0.0859 | 0.0574 | 0.0078 | -0.0304 | 0.0303 |
| 0.0398 | 0.0876 | 0.0816 | 0.9142 | 0.6993 | 0.6934 | 0.6150 | 0.5287 | 0.3245 | 0.2225 |
| 0.2019 | 0.1623 | 0.1238 | 0.0499 | 0.0627 | 0.1651 | 0.0441 | 0.1827 | 0.0997 | 0.7784 |
| 0.3950 | 0.1172 | 0.1048 | 0.2090 | 0.2065 | 0.4447 | 0.1835 | 0.1413 | 0.1717 | 0.2090 |
| 0.2422 | 0.2963 | 0.5218 | 0.4374 | 0.4020 | 0.3907 | 0.4526 | 0.3484 | 0.2882 | 0.2850 |
| 0.1551 | 0.1446 | -0.0076 | -0.0848 | -0.0420 | 0.0092 | 0.0390 | 0.0860 | 0.8249 | 0.2451 |
| 0.7696 | 0.3708 | 0.1170 | 0.2570 | 0.5104 | | | | | |

Figure. 14

Table 9. The testing samples of influent TP (mg/L)

| | | | | | | | | |
|---|---|---|---|---|---|---|---|---|
| 3.9522 | 4.1867 | 4.5942 | 4.5057 | 4.5057 | 4.0066 | 3.7529 | 4.1116 | 4.1465 | 4.1465 |
| 4.1465 | 4.0993 | 4.2017 | 4.5199 | 4.1266 | 4.2198 | 3.4877 | 4.7860 | 3.9951 | 4.3522 |
| 4.4541 | 4.1859 | 4.2168 | 3.9868 | 3.9029 | 4.0702 | 4.1378 | 4.3289 | 4.3061 | 4.0605 |
| 4.1268 | 3.9708 | 3.9485 | 4.0112 | 4.1164 | 4.3104 | 4.0388 | 3.8027 | 3.7678 | 4.0382 |
| 4.2339 | 4.2524 | 4.1057 | 3.9310 | 3.9415 | 3.8455 | 4.3598 | 4.2394 | 4.2394 | 4.2394 |
| 4.2394 | 4.2392 | 4.2392 | 4.2392 | 4.2889 | 3.9926 | 4.1127 | 4.0208 | 4.1534 | 4.2663 |
| 4.2058 | 4.0359 | 3.8457 | 3.7628 | 3.9413 | 4.0122 | 3.9671 | 3.9380 | 3.9573 | 3.7158 |
| 3.6388 | 3.6132 | 3.8164 | 3.9993 | 3.9670 | 4.0034 | 4.1387 | 4.1678 | 3.9797 | 4.2248 |

Table 10. The testing samples of temperature (°C)

| | | | | | | | | |
|---|---|---|---|---|---|---|---|---|
| 27.3334 | 27.2888 | 27.1983 | 27.0192 | 26.7961 | 26.7136 | 27.0384 | 27.2132 | 27.1539 | 27.0562 |
| 26.9083 | 26.7740 | 26.6502 | 26.0400 | 25.9641 | 25.8663 | 25.6143 | 25.6740 | 25.0187 | 25.2400 |
| 25.2516 | 25.2849 | 24.9667 | 24.8960 | 24.9797 | 24.9436 | 24.9018 | 24.8513 | 24.7577 | 24.6598 |
| 24.6368 | 24.8153 | 25.1604 | 25.1300 | 25.0664 | 24.9523 | 24.8095 | 24.5131 | 24.4355 | 24.3796 |
| 24.2463 | 24.1375 | 23.9473 | 23.7390 | 23.8631 | 24.2047 | 24.3165 | 24.2836 | 24.1933 | 23.9531 |
| 23.7277 | 24.1163 | 23.8377 | 23.6623 | 23.6295 | 23.6253 | 23.6224 | 23.5769 | 23.4745 | 23.3310 |
| 23.1451 | 23.0007 | 23.0191 | 23.1409 | 23.1565 | 23.1551 | 23.1027 | 22.9738 | 22.8098 | 22.7504 |
| 23.0191 | 23.4446 | 23.6680 | 23.7393 | 23.7193 | 23.6096 | 23.4489 | 23.3949 | 23.4915 | 23.8662 |

Figure. 15

Table 11. The testing samples of ORP in anaerobic terminal

| | | | | | | | | |
|---|---|---|---|---|---|---|---|---|
| 552.1540 | 568.8970 | 551.9620 | 552.6030 | 558.6280 | 561.4480 | 543.7580 | 565.7420 | 565.0370 | 564.2680 |
| 565.2930 | 564.3960 | 565.9980 | 489.0880 | 558.1790 | 558.8200 | 487.6130 | 568.9460 | 565.5500 | 580.4190 |
| 581.5730 | 581.7010 | 582.0850 | 581.1830 | 580.0980 | 579.7780 | 580.6110 | 580.7390 | 580.1630 | 579.8420 |
| 578.1120 | 579.3930 | 578.2400 | 578.1760 | 577.5990 | 577.0860 | 576.7020 | 573.6890 | 574.7150 | 574.7790 |
| 575.0350 | 572.1510 | 572.8560 | 571.6380 | 573.7530 | 574.0100 | 575.3560 | 575.2920 | 574.8430 | 574.0100 |
| 573.7530 | 574.5860 | 573.9460 | 573.3050 | 570.4210 | 570.0360 | 572.0230 | 572.2150 | 573.4970 | 572.9840 |
| 572.9840 | 573.3050 | 577.3420 | 578.5600 | 570.6130 | 571.5740 | 570.9970 | 569.9080 | 567.6650 | 569.0100 |
| 569.3310 | 569.4590 | 570.6130 | 572.8560 | 571.4460 | 570.6130 | 569.8440 | 569.3950 | 570.2920 | 571.1900 |

Table 12. The testing samples of DO in front of aerobic (mg/L)

| | | | | | | | | |
|---|---|---|---|---|---|---|---|---|
| 0.0383 | 0.0428 | 0.0361 | 0.0378 | 0.0395 | 0.0602 | 0.0706 | 0.0453 | 0.0743 | 0.0735 |
| 0.0567 | 0.1172 | 0.0582 | 0.0398 | 0.0609 | 0.0811 | 0.0686 | 0.0398 | 0.0474 | 0.0317 |
| 0.0298 | 0.1265 | 0.0659 | 0.0971 | 0.0345 | 0.0355 | 0.0457 | 0.0488 | 0.0412 | 0.0545 |
| 0.0765 | 0.0364 | 0.0406 | 0.0843 | 0.0464 | 0.0346 | 0.1481 | 0.4026 | 0.3942 | 0.4193 |
| 0.4073 | 0.4379 | 0.5426 | 0.5498 | 0.8550 | 0.4892 | 0.4207 | 0.4564 | 0.4889 | 0.5378 |
| 0.5400 | 0.5287 | 0.5440 | 0.5110 | 0.8817 | 0.8742 | 0.4291 | 0.4537 | 0.3765 | 0.3696 |
| 0.3782 | 0.3274 | 0.7197 | 0.5351 | 0.2611 | 0.3343 | 0.3412 | 0.3301 | 0.2746 | 0.2365 |
| 0.3272 | 0.2974 | 0.2066 | 0.1995 | 0.2546 | 0.2459 | 0.2654 | 0.2566 | 0.2232 | 0.2282 |

Figure. 16

Table 13. The testing samples of TSS in aerobic terminal (mg/L)

| 2.8343 | 2.8151 | 2.7787 | 2.7807 | 2.7539 | 2.7827 | 2.8063 | 2.8055 | 2.9044 | 2.8029 |
|---|---|---|---|---|---|---|---|---|---|
| 2.7963 | 2.8936 | 2.8786 | 2.8337 | 2.7973 | 2.7974 | 2.8266 | 2.8632 | 2.9151 | 2.7774 |
| 2.8432 | 2.7067 | 2.6005 | 2.6635 | 2.5869 | 2.5829 | 2.5363 | 2.5279 | 2.4897 | 2.4674 |
| 2.4916 | 2.5265 | 2.5397 | 2.4082 | 2.4903 | 2.3932 | 2.4240 | 2.4906 | 2.5340 | 2.3839 |
| 2.4320 | 2.3993 | 2.5394 | 2.5140 | 2.4693 | 2.4245 | 2.4605 | 2.4649 | 2.3919 | 2.4472 |
| 2.4740 | 2.4481 | 2.5045 | 2.4331 | 2.4866 | 2.5113 | 2.4309 | 2.3655 | 2.3883 | 2.2805 |
| 2.3078 | 2.2824 | 2.2668 | 2.2297 | 2.2105 | 2.4196 | 2.2935 | 2.3671 | 2.3100 | 2.3821 |
| 2.4491 | 2.5777 | 2.4440 | 2.4318 | 2.4089 | 2.4784 | 2.4254 | 2.4256 | 2.3243 | 2.3120 |

Table 14. The testing samples of effluent pH

| 7.9298 | 7.9087 | 7.8818 | 7.8386 | 7.8445 | 7.8517 | 7.8622 | 7.8667 | 7.8590 | 7.8593 |
|---|---|---|---|---|---|---|---|---|---|
| 7.8643 | 7.8702 | 7.9216 | 7.9536 | 7.9188 | 7.9032 | 7.8936 | 8.0238 | 8.0090 | 7.9940 |
| 8.0011 | 8.0101 | 7.9908 | 7.9930 | 7.9959 | 7.9983 | 8.0112 | 8.0045 | 7.9968 | 7.9936 |
| 7.9866 | 8.0030 | 8.0069 | 7.9992 | 8.0040 | 8.0033 | 8.0015 | 8.0090 | 8.0264 | 8.0254 |
| 8.0373 | 8.0021 | 8.0281 | 8.0288 | 8.0305 | 8.0431 | 8.0480 | 8.0316 | 8.0184 | 8.0091 |
| 8.0132 | 8.0151 | 8.0128 | 7.9982 | 8.0055 | 8.0419 | 8.0627 | 8.0595 | 8.0498 | 8.0158 |
| 8.0107 | 8.0120 | 8.0195 | 8.0314 | 8.0187 | 8.0398 | 8.0368 | 8.0281 | 7.9850 | 8.0196 |
| 8.0101 | 8.0212 | 8.0334 | 8.0235 | 8.0123 | 8.0105 | 8.0145 | 8.0124 | 8.0209 | 8.0745 |

Figure. 17

Table 15. The testing samples of real effluent TP (mg/L)

| 2.2080 | 2.8100 | 2.9440 | 3.2380 | 3.4340 | 2.3920 | 2.2340 | 2.5820 | 2.7780 | 2.7180 |
|---|---|---|---|---|---|---|---|---|---|
| 2.9820 | 2.9980 | 2.9660 | 2.6980 | 2.6280 | 2.8020 | 2.8760 | 2.7600 | 1.9180 | 1.5360 |
| 1.2100 | 0.2880 | 0.2480 | 0.2060 | 0.1880 | 0.1700 | 0.1920 | 0.1700 | 0.1820 | 0.1840 |
| 0.2320 | 0.6300 | 0.1660 | 0.1760 | 0.1740 | 0.1920 | 0.1780 | 0.1940 | 0.1760 | 0.1620 |
| 0.1580 | 0.2400 | 0.2280 | 0.2240 | 0.1640 | 0.1660 | 0.1520 | 0.1580 | 0.1520 | 0.1700 |
| 0.1720 | 0.1500 | 0.1520 | 0.3680 | 0.3720 | 0.2340 | 0.1880 | 0.1700 | 0.1740 | 0.1860 |
| 0.2120 | 0.2240 | 0.2700 | 0.2700 | 0.2800 | 0.2740 | 0.1540 | 0.1520 | 0.2520 | 0.1920 |
| 0.1480 | 0.1460 | 0.1520 | 0.1480 | 0.1540 | 0.1700 | 0.1740 | 0.1960 | 0.1820 | 0.1860 |

Table 16. The outputs of PSO-SORBF neural network in the testing process

| 2.612147 | 2.771787 | 3.0175 | 3.10406 | 3.1241 | 2.890512 | 2.788423 | 2.955665 | 2.977487 | 2.949753 |
|---|---|---|---|---|---|---|---|---|---|
| 2.901283 | 2.76904 | 2.511406 | 2.43037 | 2.295532 | 2.373796 | 2.392996 | 1.882943 | 1.530693 | 1.236367 |
| 1.424638 | 0.793371 | 0.424218 | 0.474996 | 0.475561 | 0.424892 | 0.245951 | 0.327077 | 0.249549 | 0.036324 |
| 0.150432 | 0.238796 | 0.530201 | 0.325941 | 0.418546 | 0.437621 | 0.079248 | 0.103571 | 0.135899 | -0.08638 |
| 0.006305 | 0.051586 | 0.150304 | 0.015725 | 0.415903 | 0.082866 | 0.211118 | 0.025616 | -0.002448 | 0.041199 |
| 0.077956 | 0.025702 | 0.100086 | 0.061381 | 0.616359 | 0.54136 | 0.226834 | 0.187348 | 0.092187 | 0.127787 |
| 0.120912 | 0.13303 | 0.292555 | 0.14985 | 0.289318 | 0.147976 | 0.211324 | 0.226368 | 0.456698 | 0.421796 |
| 0.361888 | 0.416812 | 0.151583 | -0.04443 | -0.03413 | 0.05616 | 0.099968 | 0.145411 | 0.098177 | 0.435992 |

Figure. 18

MEASURING PHOSPHORUS IN WASTEWATER USING A SELF-ORGANIZING RBF NEURAL NETWORK

CROSS-REFERENCE TO RELATED PATENT APPLICATIONS

This application is a continuation in part of a U.S. patent application Ser. No. 14/620,088, filed on Nov. 2, 2015 titled "Measuring Phosphorus in Wastewater Using a Self-Organizing RBF Neural Network", which claims priority to Chinese Patent Application No. 201410602859.X, filed on Nov. 2, 2014, entitled "a Soft-Computing Method for the Effluent Total Phosphorus Based on a Self-Organizing PSO-RBF Neural Network," which is hereby incorporated by reference in its entirety.

TECHNICAL FIELD

Implementations here related to control environment engineering, more specifically related to methods and systems for determining effluent total phosphorus (TP) concentrations in the urban wastewater treatment process (WWTP).

BACKGROUND

Biogeochemical characteristics of phosphorus play a significant role in eutrophication processes. Phosphorus may accumulate in lake sediments during heavy loading periods and release from sediments into the overlying water after the external loading is reduced. The released phosphorus sustains the eutrophication processes and cycles between overlying water and sediments through algal growth, organic deposition, decomposition, and release. Therefore, phosphorus is generally recognized as the limiting factor in the process of eutrophication. Restoration efforts to control phosphorus from WWTP into rivers are considered to be important strategies for decreasing cyanobacterial risks in the environment.

To reduce levels of phosphate, some design principles and various mechanisms are recently adopted to produce low effluent TP concentrations in urban WWTP. The effluent TP concentration is an index of water qualities in the urban WWTP. However, using conventional technologies, it is difficult to timely estimate the effluent TP concentration under closed-loop control. The timely and/or online detection technology of effluent TP concentrations is a bottleneck for the control of the urban WWTP. Moreover, the real-time information of effluent TP concentrations can enhance the quality monitoring level and alleviate the current situation of wastewater to strengthen the whole management of WWTP. Therefore, the timely detection of effluent TP concentration owns both great economic benefit and environmental benefit.

Methods for monitoring the effluent TP concentration may include spectrophotometry method, gas chromatography method, a liquid chromatography method, electrode method, and mechanism model. However, the spectrophotometry method, gas chromatography method, liquid chromatography method and electrode method rely upon previously collected data analysis of primary variables. Some of the variables, such as gas chromatography method, require more than 30 minutes to obtain. This makes these approaches inadequate for real-time and/or online monitoring. The mechanism model studies the phosphorus dynamics to obtain the effluent TP concentration online based on the biogeochemical characteristics of phosphorus. However, significant errors may be incurred in the measurement of effluent TP concentrations. Moreover, because of the different conditions of every urban WWTP, a common model is difficult to be determined. Thus, technologies for timely monitoring effluent TP concentrations are not well developed.

SUMMARY

Methods and systems are designed for effluent TP concentrations based on a PSO-SORBF neural network in various implementations. In various implements, the inputs are those variables that are easy to measure, and the outputs are estimates of the effluent TP concentration. Since the input-output relationship is encoded in the data used to calibrate the model, a method is used to reconstruct it and then to estimate the output variables. In general, the procedure of soft-computing method comprises three parts: data acquisition, data pre-processing and model design. For various implementations, the experimental hardware is set up. The historical process data are routinely acquired and stored in the data acquisition system. The data may be easily retrieved by the method. The variables whose data are easy to measure by the instruments comprise: influent TP, oxidation-reduction potential (ORP) in the anaerobic tank, dissolved oxygen (DO) concentration in the aerobic tank, temperature in the aerobic tank, total suspended solids (TSS) in the aerobic tank, effluent pH, chemical oxygen demand (COD) concentration in the aerobic tank and total nutrients (TN) concentration in the aerobic tank. Then, data pre-processing and model design is developed to predict the effluent TP concentrations.

Various implementations adopt the following technical scheme and implementation steps:

A soft-computing method for the effluent TP concentration based on a PSO-SORBF neural network, its characteristic and steps include the following steps: (1) Selecting input variables, (2) Initializing the PSO-SORBF neural network, (3) training the PSO-SORBF neural network, and (4) setting the PSO-SORBF neural network.

(1) Select Input Variables

Remarkable characteristics of the data acquired in urban WWTP are redundancy and possibly insignificance. And the choice of the input variables that influence the model output is a crucial stage. Therefore, it is necessary to select the suitable input variables and prepare their data before using the soft-computing method. Moreover, variable selection comprises choosing those easy to measure variables that are most informative for the process being modeled, as well as those that provide the highest generalization ability. In various implementations, the partial least squares (PLS) method is used to extract the input variables for the soft-computing method.

In various implementations, a history data set {X, y} is used for the variable selection. Since the variables acquired from experimental hardware are influent TP, ORP, DO, temperature, TSS, effluent pH, COD, and TN. X is a n×8 process variable matrix, and y is the dependent n×1 variable vector. The PLS method can model both outer and inner relations between X and y. For the PLS method, X and y may be described as:

$$X = TP^T + E = \sum_{i=1}^{8} t_i p_i^T + E, \quad (1)$$

-continued $$y = UQ^T + F = \sum_{i=1}^{8} u_i q_i^T + F,$$

where T, P, and E are the score matrix, loading matrix and residual matrix of X, respectively. U, Q, and F are the score matrix, loading matrix and residual matrix of y. $t_i$, $p_i$, $u_i$, and $q_i$ are the vectors of T, P, U and Q. In addition, the inner relationship between X and y is shown as follow:

$$\hat{u}_i = b_i t_i,$$

$$b_i = u_i^T t_i / t_i^T t_i, \qquad (2)$$

where i=1, 2, ..., 8, $b_i$ is the regression coefficients between the $t_i$ from X and $u_i$ from y. Then, the cross-validation values for the components in X and y are described as:

$$R_i = G_i / G, \quad i = 1, 2, L, 8; \qquad (3)$$

$$G = \sum_{i=1}^{8} \|\hat{u}_i - t_i\|,$$

$$G_i = \|\hat{u}_i - t_i\|,$$

if $R_i < \xi$, $\xi \in (0, 0.1)$, the ith component is the right input variable for the soft-computing model. Based on the PLS method, the selected input variables are influent TP, ORP, DO, T, TSS and effluent pH in various implementations.

(2) Initialize the PSO-SORBF Neural Network

The initial structure of PSO-SORBF neural network comprises three layers: input layer, hidden layer, and output layer. There are 6 neurons in the input layer, K neurons in the hidden layer and 1 neuron in the output layer, K>2 is a positive integer. The number of training samples is T. The input vector of PSO-SORBF neural network is $x(t)=[x_1(t), x_2(t), x_3(t), x_4(t), x_5(t), x_6(t)]$ at time t. $x_1(t)$ is the value of influent TP, $x_2(t)$ is the value of ORP, $x_3(t)$ is the value of DO, $x_4(t)$ is the value of temperature, $x_5(t)$ is the value of TSS, and $x_6(t)$ is the value of effluent pH at time t respectively. y(t) is the output of PSO-SORBF neural network, and $y_d(t)$ is the real value of effluent TP concentration at time t respectively. The output of PSO-SORBF neural network may be described:

$$y(t) = \sum_{k=1}^{K} w_k(t) \phi_k(x(t)), \qquad (4)$$

where $w_k$ is the output weight between the kth hidden neuron and the output neuron, k=1, 2, ..., K, K is the number of hidden neurons, and $\phi_k$ is the RBF of kth hidden neuron which is usually defined by a normalized Gaussian function:

$$\phi_k(x(t)) = e^{(-\|x(t) - \mu_k(t)\|^2 / 2\sigma_k^2(t))}, \qquad (5)$$

$\mu_k = [\mu_{k,1}, \mu_{k,2}, \ldots, \mu_{k,6}]$ denotes the center vector of the kth hidden neuron, $\sigma_k$ is the width of the kth hidden neuron, $\|x(t) - \mu_k(t)\|$ is the Euclidean distance between x(t) and $\rho_k(t)$.

(3) Train the PSO-SORBF Neural Network

① Initialize the acceleration constants $c_1$ and $c_2$, $c_1 \in (0, 1)$, $c_2 \in (0, 1)$, and the balance factor $\alpha \in [0, 1]$. During the particle initialization stage, let the position of the ith particle in the searching space be represented as:

$$a_i = [\mu_{i,1}, \sigma_{i,1}, w_{i,1}, \mu_{i,2}, \sigma_{i,2}, w_{i,2} L \mu_{i,K_i}, \sigma_{i,K_i}, w_{i,K_i}], \qquad (6)$$

where $a_i$ is the position of an ith particle, i=1, 2, ..., s, and s is the total number of particles, s>2 is a positive integer. $\mu_{i,k} = [\mu_{i,k,1}, \mu_{i,k,2}, \ldots, \mu_{i,k,6}]$, $\sigma_{i,k}$, $w_{i,k}$ are the center, width and output weight of the kth hidden neuron in the ith particle, and the initial values are $\|\mu_{i,k}\| < 1$, $\sigma_{i,k} \in (0, 1)$, $w_{i,k} \in (0, 1)$. $K_i$ is the number of hidden neurons in the ith particle. Simultaneously, initialize the velocity of particle:

$$v_i = [v_{i,1}, v_{i,2}, L v_{i,D_i}], \qquad (7)$$

where $v_i$ is the velocity of the ith particle, $D_i$ is the dimension of the ith particle and $D_i = 3K_i$.

② From the input of neural network x(t) and the dimensions $D_i$ of each particle, the fitness value of each particle may be calculated:

$$f(a_i(t)) = E_i(t) + \alpha K_i(t), \qquad (8)$$

where $$E_i(t) = \sqrt{\frac{1}{2T} \sum_{t=1}^{T} (y(t) - y_d(t))^2}, \qquad (9)$$

i=1, 2, ..., s, $K_i(t)$ is the number of hidden neurons in the ith particle at time t, T is the number of the training samples.

③ Calculate the inertia weight of each particle:

$$\omega_i(t) = \gamma(t) A_i(t), \qquad (10)$$

where $\omega_i(t)$ is the inertia weight of the ith particle at time t, and $$\gamma(t) = (C - S(t)/1000)^{-t},$$

$$S(t) = f_{min}(a(t))/f_{max}(a(t)),$$

$$A_i(t) = f(g(t))/f(a_i(t)), \qquad (11)$$

C is a constant, and $C \in [1, 5]$, $f_{min}(a(t))$, $f_{max}(a(t))$ are the minimum fitness value and the maximum fitness value at time t, and $g(t) = [g_1(t), g_2(t), \ldots, g_D(t)]$ is the global best position, $f_{min}(a(t))$, $f_{max}(a(t))$ and g(t) may be expressed as:

$$\begin{cases} f_{min}(a(t)) = \text{Min}(f(a_i(t))) \\ f_{max}(a(t)) = \text{Max}(f(a_i(t))) \end{cases}, \qquad (12)$$

$$g(t) = \underset{p_i}{\text{argmin}}(f(p_i(t))), \ 1 \leq i \leq s,$$

where $p_i(t) = [p_{i,1}(t), p_{i,2}, \ldots, p_{i,D}(t)]$ is the best position of the ith particle:

$$p_i(t+1) = \begin{cases} p_i(t), & \text{if } f(a_i(t+1)) \geq f(p_i(t)) \\ a_i(t+1), & \text{otherwise} \end{cases}. \qquad (13)$$

④ Update the position and velocity of each particle:

$$v_{i,d}(t+1) = \omega v_{i,d}(t) + c_1 r_1 (p_{i,d}(t) - a_{i,d}(t)) + c_2 r_2 (g_d(t) - a_{i,d}(t)), \qquad (14)$$

$$g(t) = \underset{p_i}{\text{argmin}}(f(p_i(t))), \ 1 \leq i \leq s,$$

where $r_1$ and $r_2$ are the coefficients of the particle and global best position respectively, $r_1 \in [0, 1]$ and $r_2 \in [0, 1]$.

⑤ Search the best number of hidden neurons $K_{best}$ according to the global best position g(t), and update the number of hidden neurons in the particles:

$$K_i = \begin{cases} K_i - 1 & \text{if } (K_{best} < K_i) \\ K_i + 1 & \text{if } (K_{best} \geq K_i) \end{cases}. \quad (15)$$

⑥ Import the training sample x(t+1), and repeat the steps ②-⑤, then, stop the training process after all of the training samples are imported into the neural network.
(4) The Testing Samples are then Set to the Trained PSO-SORBF Neural Network.

The outputs of PSO-SORBF neural network is the predicting values of effluent TP concentration. Moreover, the program of this soft-computing method has been designed based on the former analysis. The program environment of the proposed soft-computing method comprises a Windows 8 64-bit operating system, a clock speed of 2.6 GHz and 4 GB of RAM. And the program is based on the Matlab 2010 under the operating system.

In some implementations, in order to detect the effluent TP concentration online and with acceptable accuracy, a method is developed in various implementations. The results demonstrate that the effluent TP trends in WWTP may be predicted with acceptable accuracy using the influent TP, ORP, DO, temperature, TSS, and effluent pH data as input variables. This soft-computing method can predict the effluent TP concentration with acceptable accuracy and solve the problem that the effluent TP concentration is difficult to be measured online.

This method is based on the PSO-SORBF neural network in various implementations, which is able to optimize both the parameters and the network size during the learning process simultaneously. The advantages of the proposed PSO-SORBF neural network are that it can simplify and accelerate the structure optimization process of the RBF neural network and can predict the effluent TP concentration accurately. Moreover, the predicting performance shows that the PSO-SORBF neural network-based soft-computing method can match system nonlinear dynamics. Therefore, this soft-computing method performs well in the whole operating space.

Various implementations utilize six input variables in this soft-computing method to predict the effluent TP concentration. In fact, it is in the scope of various implementations that any of the variables: the influent TP, ORP, DO, temperature, TSS, effluent pH, COD, and TN, are used to predict the effluent TP concentration. Moreover, this soft-computing method is also able to predict the other variables in urban WWTP.

BRIEF DESCRIPTION OF THE DRAWINGS

The detailed description is described with reference to the accompanying figures.

FIGS. 7-18 show tables 1-16 including experimental data of various implementations.

DETAILED DESCRIPTION

Figure 1:
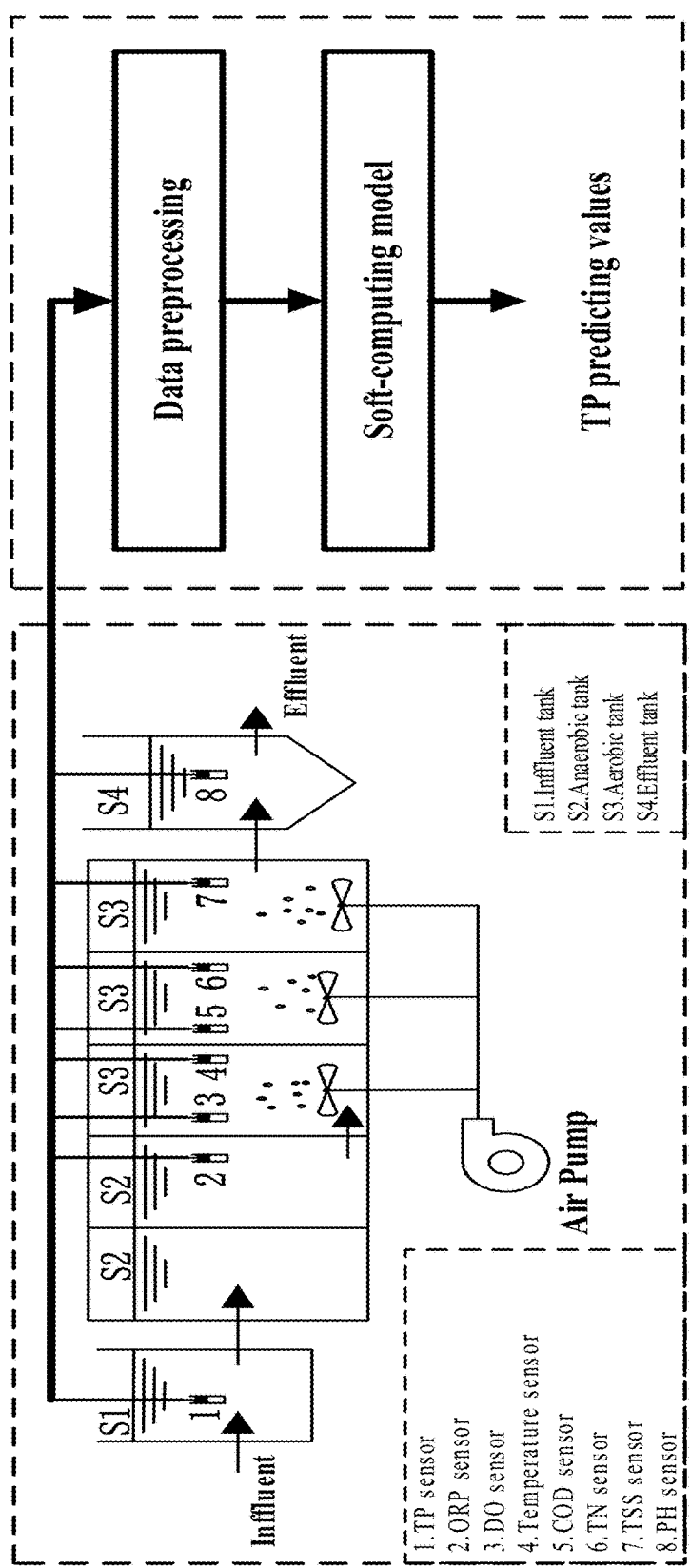
FIG. 1 shows the overall flow chart of a method for predicting effluent TP concentration in various implementations.

Various implementations of methods and systems are developed to predict the effluent TP concentration based on a PSO-SORBF neural network in various implementations. For the implementations, inputs of the neural network are variables that are easy to measure, and outputs of the neural network are estimates of the effluent TP concentration. In general, the procedure of soft-computing method comprises three parts: data acquisition, data pre-processing and model design. For various implementations, the experimental hardware is set up as shown in FIG. 1. The historical process data are routinely acquired and stored in the data acquisition system. The data may be easily retrieved. The variables whose data are easy to measure by the instruments comprise: influent TP, ORP in the anaerobic tank, DO concentration in the aerobic tank, the temperature in the aerobic tank, TSS in the aerobic tank, effluent pH, COD concentration in the aerobic tank and TN concentration in the aerobic tank. Then, data pre-processing and model design is developed to predict the effluent TP concentration.

Various implementations adopt the following technical scheme and implementation steps for the effluent TP concentration based on a PSO-SORBF neural network. The characteristic and steps are described as follow.
(1) Select Input Variables Remarkable characteristics of the data acquired in urban WWTP are redundancy and possibly insignificance. And the choice of the input variables that influence the model output is a crucial stage. Therefore, it is necessary to select the suitable input variables and prepare their data before using the soft-computing method. Moreover, variable selection comprises choosing those easy to measure variables that are most informative for the process being modeled, as well as those that provide the highest generalization ability. In various implementations, the PLS method is used to extract the input variables for the soft-computing method.

The experimental data were obtained from an urban WWTP in 2014. There are 245 groups of samples which are divided into two parts: 165 groups of training samples and 80 groups of testing samples.

In various implementations, a history data set {X, y} is used for variable selection. Since the variables acquired from experimental hardware are influent TP, ORP, DO, temperature, TSS, effluent pH, COD and TN. X is a 165×8 process variable matrix, and y is the dependent 165×1 variable vector. The PLS method can model both outer and inner relations between X and y. For the PLS method, X and y may be described as follows:

$$X = TP^T + E = \sum_{i=1}^{8} t_i p_i^T + E, \quad (16)$$

$$y = UQ^T + F = \sum_{i=1}^{8} u_i q_i^T + F,$$

where T, P and E are the score matrix, loading matrix and residual matrix of X, respectively. U, Q and F are the score matrix, loading matrix and residual matrix of y. $t_i$, $p_i$, $u_i$ and $q_i$ are the vectors of T, P, U and Q. In addition, the inner relationship between X and y is shown as follow:

$$\hat{u}_i = b_i t_i,$$

$$b_i = u_i^T t_i / t_i^T t_i, \quad (17)$$

where $i=1, 2, \ldots, 8$, $b_i$ is the regression coefficients between the $t_i$ from X and $u_i$ from y. Then, the cross-validation values for the components in X and y are described as:

$$R_i = G_i / G, \quad i = 1, 2, L, 8; \quad (18)$$

$$G = \sum_{i=1}^{8} \|\hat{u}_i - t_i\|,$$

$$G_i = \|\hat{u}_i - t_i\|,$$

if $R_i < \xi$, $\xi = 0.01$, the ith component is the right input variable for the soft-computing model. Based on the PLS method, the selected input variables are influent TP, ORP, DO, T, TSS and effluent pH in various implementations.

(2) Initialize the PSO-SORBF Neural Network

Figure 2:
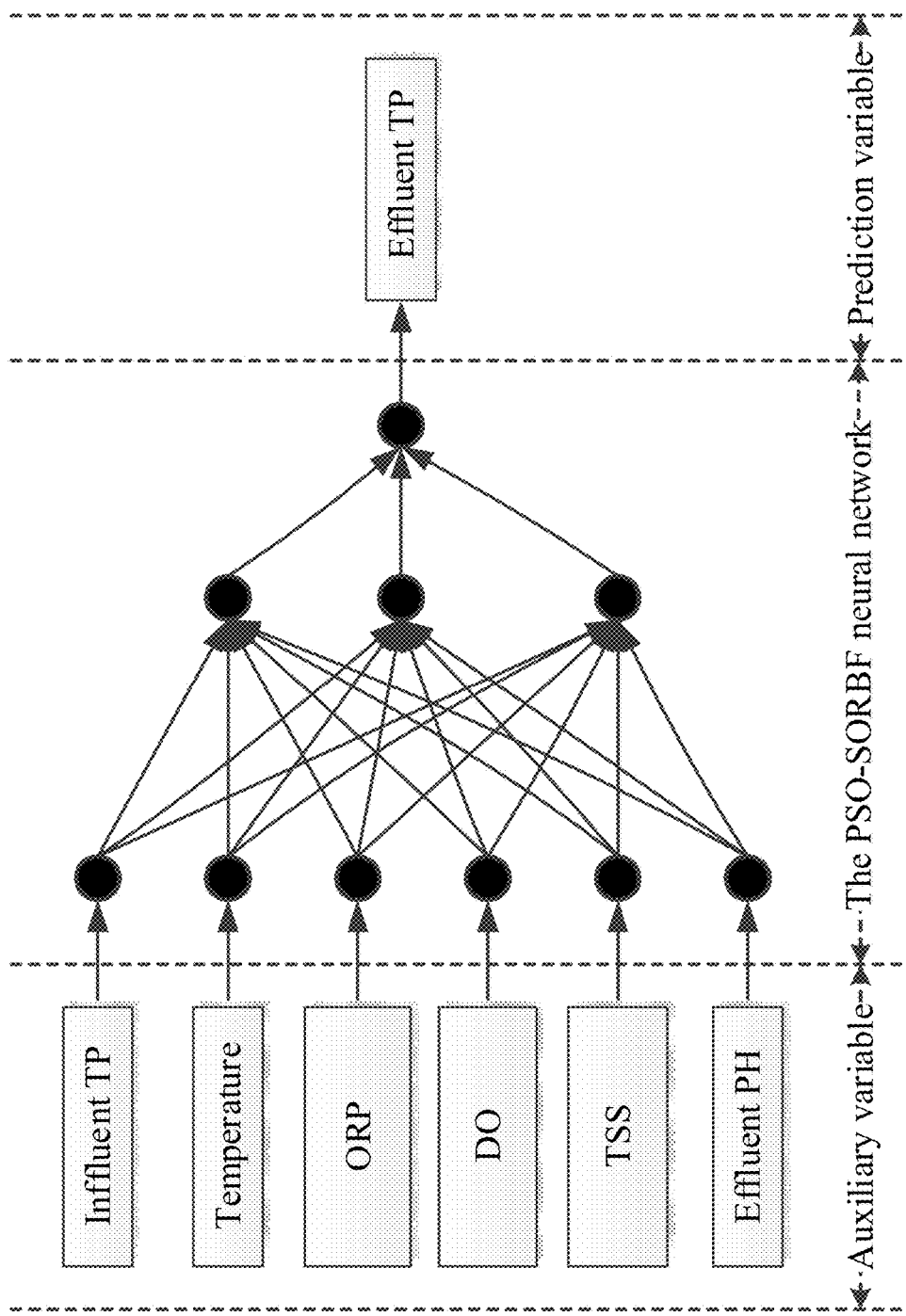
FIG. 2 shows the structure of PSO-SORBF neural network in various implementations.

The initial structure of PSO-SORBF neural network, which is shown in FIG. 2 comprises three layers: input layer, hidden layer and output layer. There are 6 neurons in the input layer, K neurons in the hidden layer and 1 neuron in the output layer, K=3. The number of training samples is T. The input vector of PSO-SORBF neural network is $x(t) = [x_1(t), x_2(t), x_3(t), x_4(t), x_5(t), x_6(t)]$ at time t. $x_1(t)$ is the value of influent TP, $x_2(t)$ is the value of ORP, $x_3(t)$ is the value of DO, $x_4(t)$ is the value of temperature, $x_5(t)$ is the value of TSS, and $x_6(t)$ is the value of effluent pH at time t respectively. y(t) is the output of PSO-SORBF neural network, and $y_d(t)$ is the real value of effluent TP concentration at time t respectively. The output of PSO-SORBF neural network may be described as:

$$y(t) = \sum_{k=1}^{K} w_k(t) \phi_k(x(t)), \quad (19)$$

where $w_k$ is the output weight between the kth hidden neuron and the output neuron, $k=1, 2, \ldots, K$, K is the number of hidden neurons, and $\phi_k$ is the RBF of kth hidden neuron which is usually defined by a normalized Gaussian function:

$$\phi_k(x(t)) = e^{(-\|x(t) - \mu_k(t)\|^2 / 2\sigma_k^2(t))}, \quad (20)$$

$\mu_k$ denotes the center vector of the kth hidden neuron, $\sigma_k$ is the width of the kth hidden neuron, $\|x(t) - \mu_k(t)\|$ is the Euclidean distance between $x(t)$ and $\mu_k(t)$.

(3) Train the PSO-SORBF Neural Network

① Initialize the acceleration constants $c_1$ and $c_2$, $c_1 = 0.4$, $c_2 = 0.6$, and the balance factor $\alpha = 0.1$. During the particle initialization stage, let the position of the ith particle in the searching space be represented as:

$$a_i = [\mu_{i,1}, \sigma_{i,1}, w_{i,1}, \mu_{i,2}, \sigma_{i,2}, w_{i,2} L \mu_{i,K_i}, \sigma_{i,K_i}, w_{i,K_i}], \quad (21)$$

where $a_i$ is the position of ith particle, $l=1, 2, \ldots, s$, and s is the total number of particles, $s=3$ is a positive integer. $\mu_{i,k}$, $\sigma_{i,k}$, $w_{i,k}$ are the center, width and output weight of the kth hidden neuron in the ith particle, and the initial values of the center, width and output weight are randomly generated within (0, 1). $K_1 = 2$, $K_2 = 3$, $K_3 = 4$. Initialize the velocity of particle:

$$v_i = [v_{i,1}, v_{i,2}, L v_{i,D_i}], \quad (22)$$

where $v_i$ is velocity of ith particle, $D_i$ is the dimension of the ith particle, and $D_i = 3K_i$.

② From the input of neural network x(t) and the dimensions $D_i$ of each particle, the fitness value of each particle may be calculated:

$$f(a_i(t)) = E_i(t) + \alpha K_i(t), \quad (23)$$

where $$E_i(t) = \sqrt{\frac{1}{2T} \sum_{t=1}^{T} (y(t) - y_d(t))^2}, \quad (24)$$

$i=1, 2, \ldots, s$, $K_i(t)$ is the number of hidden neurons in the ith particle at time t, T is the number of the training samples.

③ Calculate the inertia weight of each particle:

$$\omega_i(t) = \gamma(t) A_i(t), \quad (25)$$

where $\omega_i(t)$ is the inertia weight of the ith particle at time t, and $$\gamma(t) = (C - S(t)/1000)^{-t},$$

$$S(t) = f_{min}(a(t))/f_{max}(a(t)),$$

$$A_i(t) = f(g(t))/f(a_i(t)), \quad (26)$$

$C=2$, $f_{min}(a(t))$, $f_{max}(a(t))$ are the minimum fitness value and the maximum fitness value, and $g(t) = [g_1(t), g_2(t), \ldots, g_D(t)]$ is the global best position, $f_{min}(a(t))$, $f_{max}(a(t))$ and $g(t)$ may be expressed as:

$$\begin{cases} f_{min}(a(t)) = \text{Min}(f(a_i(t))) \\ f_{max}(a(t)) = \text{Max}(f(a_i(t))) \end{cases}, \quad (27)$$

$$g(t) = \underset{p_i}{\text{argmin}}(f(p_i(t))), \quad 1 \leq i \leq s,$$

where $p_i(t) = [p_{i,1}(t), p_{i,2}(t), \ldots, p_{i,D}(t)]$ is the best position of the ith particle:

$$p_i(t+1) = \begin{cases} p_i(t), & \text{if } f(a_i(t+1)) \geq f(p_i(t)) \\ a_i(t+1), & \text{otherwise} \end{cases}. \quad (28)$$

④ Update the position and velocity of each particle:

$$v_{i,d}(t+1) = \omega v_{i,d}(t) + c_1 r_1 (p_{i,d}(t) - a_{i,d}(t)) + c_2 r_2 (g_d(t) - a_{i,d}(t)), \quad (29)$$

$$g(t) = \underset{p_i}{\text{argmin}}(f(p_i(t))), \quad 1 \leq i \leq s,$$

where $r_1$ and $r_2$ are the coefficient of the particle and global best position respectively, $r_1 = 0.75$ and $r_2 = 0.90$.

⑤ Search the best number of hidden neurons $K_{best}$ according to the global best position g(t), and update the number of hidden neurons in the particles:

$$K_i = \begin{cases} K_i - 1 & \text{if } (K_{best} < K_i) \\ K_i + 1 & \text{if } (K_{best} \geq K_i) \end{cases}. \quad (30)$$

⑥ Import the training sample x(t+1), and repeat the steps ②-⑤, then, stop the training process after all of the training samples are imported to the neural network.

Figure 3:
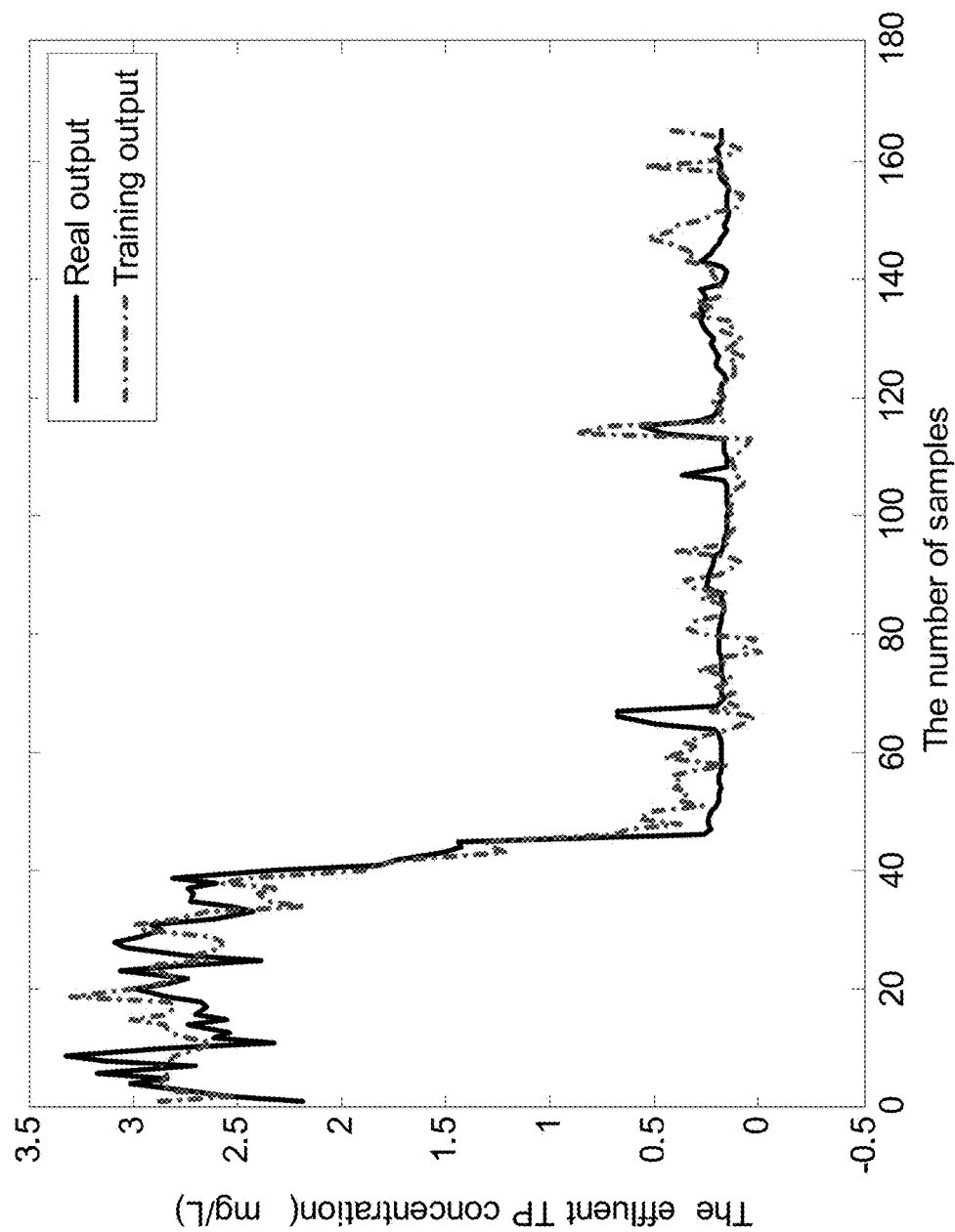
FIG. 3 shows training results of implementations.
Figure 4:
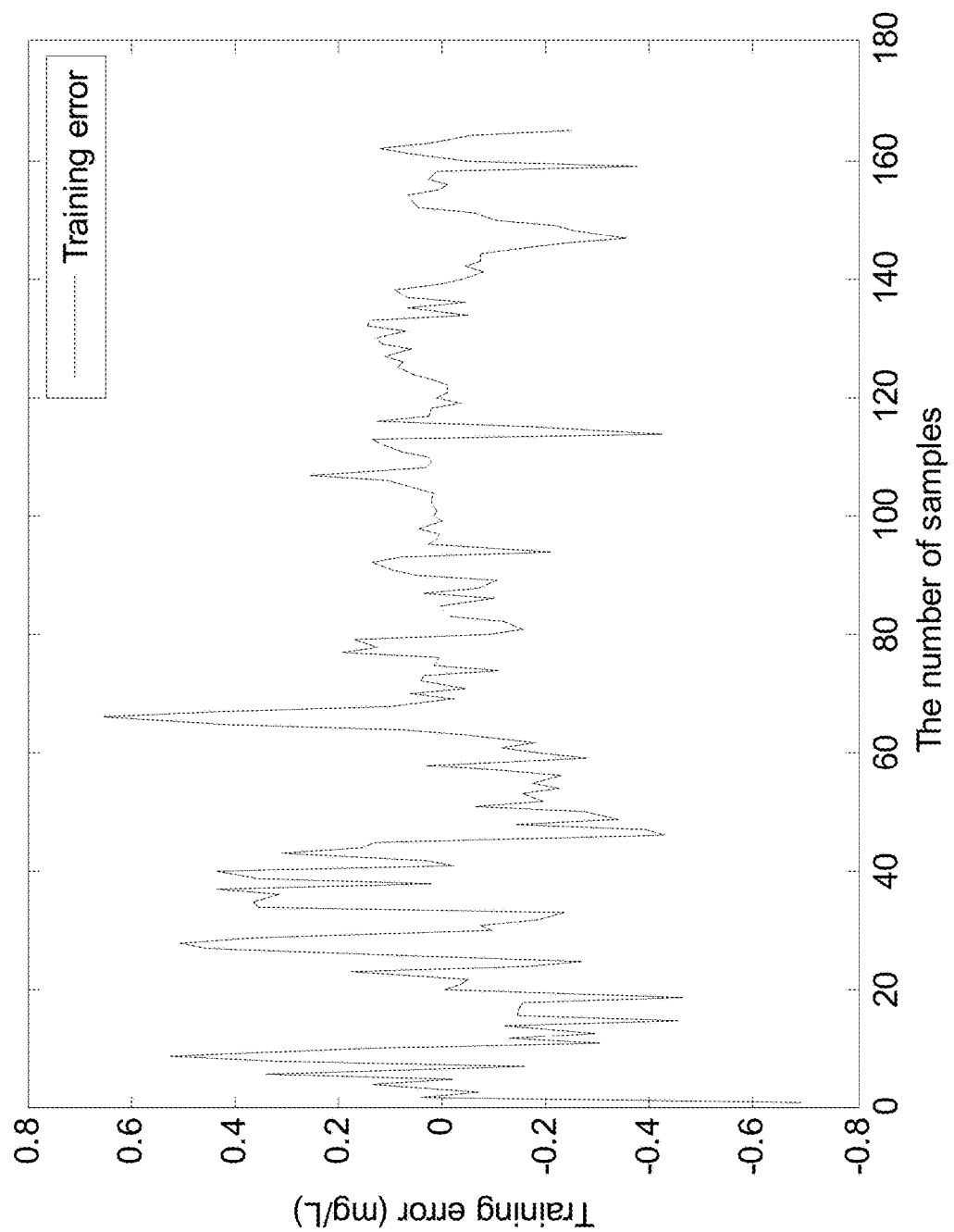
FIG. 4 shows training errors of implementations.

The training results of the soft-computing method are shown in FIG. 3. The x-axis shows the number of samples. Y-axis shows the effluent TP concentration. The unit of Y-axis is mg/L. The solid line presents the real values of effluent TP concentration. The dotted line shows the outputs of the soft-computing method in the training process. The errors between the real values and the outputs of the soft-computing method in the training process are shown in FIG. 4. The x-axis shows the number of samples. Y-axis shows the training error. The unit of Y-axis is mg/L.

Figure 5:
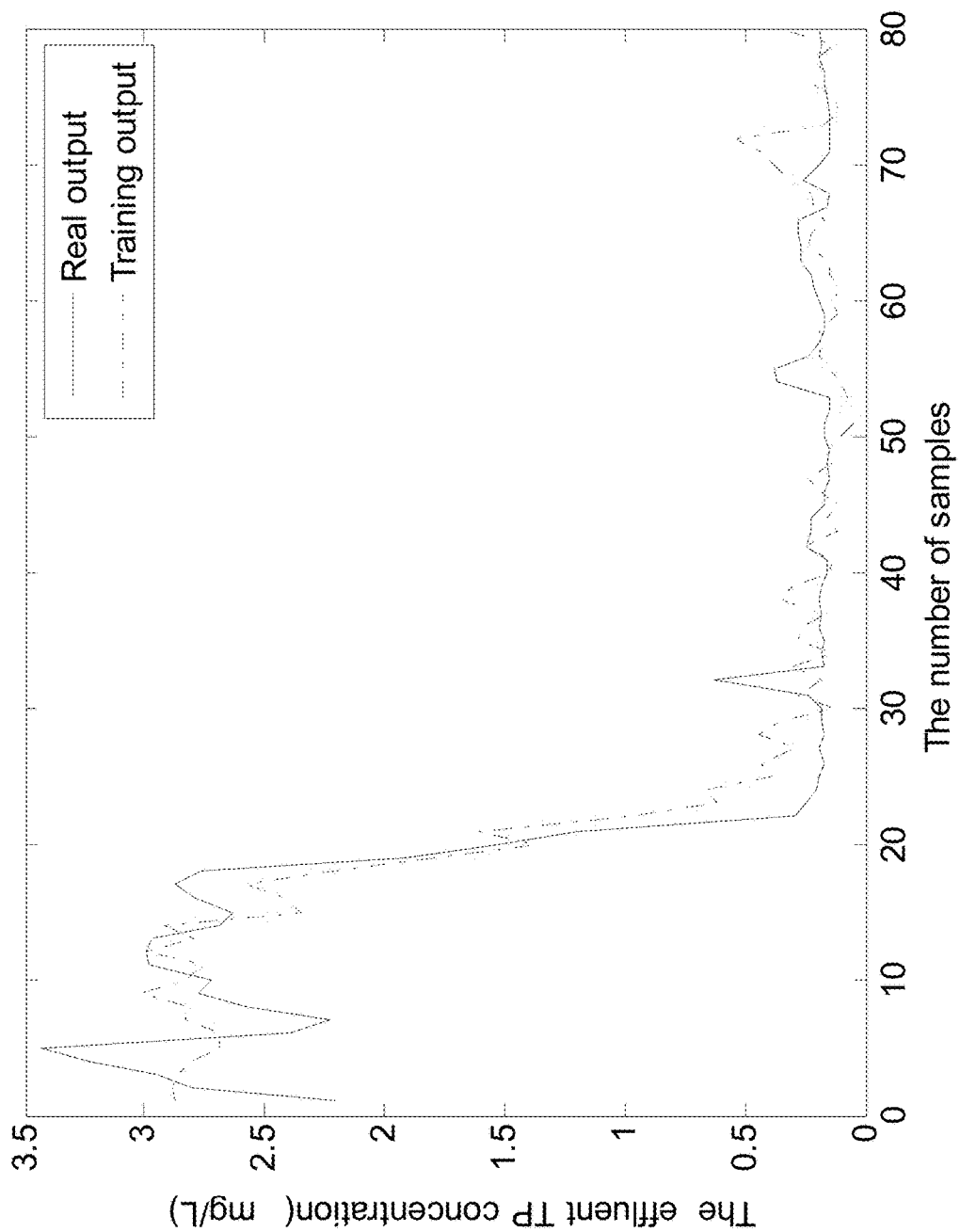
FIG. 5 shows predicting results of implementations.
Figure 6:
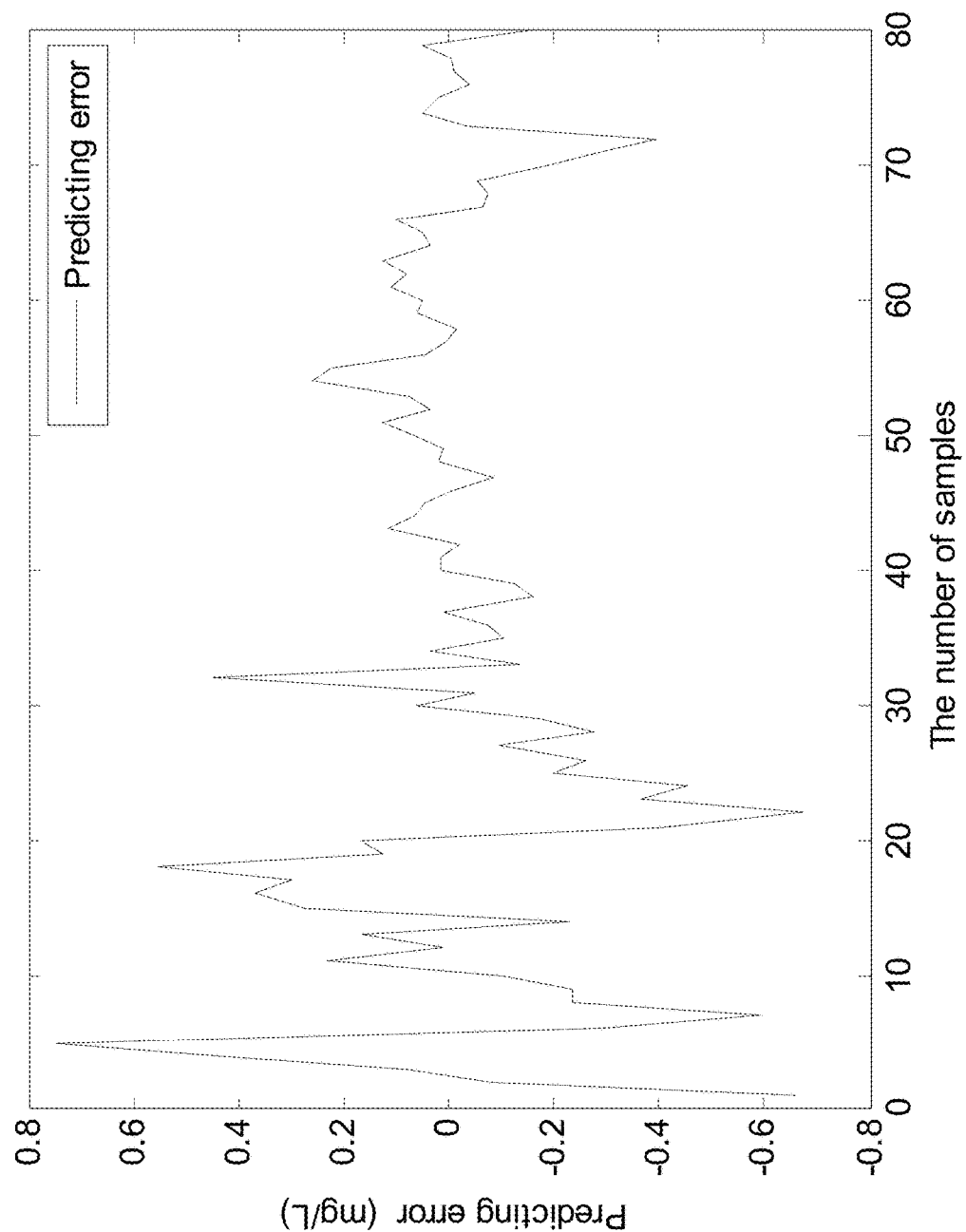
FIG. 6 shows the predicting error of implementations.

(4) The testing samples are then set to the trained PSO-SORBF neural network. The outputs of the PSO-SORBF neural network are the predicting values of effluent TP concentration. The predicting results are shown in FIG. 5. The x-axis shows the number of samples. Y-axis shows the effluent TP concentration. The unit of Y-axis is mg/L. The solid line presents the real values of effluent TP concentration. The dotted line shows the outputs of the soft-computing method in the testing process. The errors between the real values and the outputs of the soft-computing method in the testing process are shown in FIG. 6. The x-axis shows the number of samples. Y-axis shows the training error. The unit of Y-axis is mg/L.

FIGS. 7-18 show Tables 1-16 including experimental data of various implementations. Tables 1-16 show the experimental data in various implementations. Tables 1-7 show the training samples of influent TP, ORP, DO, temperature, TSS, effluent pH and real effluent TP concentration. Table 8 shows the outputs of the PSO-SORBF neural network in the training process. Tables 9-15 show the testing samples of influent TP, ORP, DO, temperature, TSS, effluent pH and real effluent TP concentration. Table 16 shows the outputs of the PSO-SORBF neural network in the predicting process. Moreover, the samples are imported as the sequence from the tables. The first data is in the first row and the first column. Then, the second data is in the first row and the second column. Until all of the data is imported from the first row, the data in the second row and following rows are inputted in the same way.

Some embodiments relate to a system for measuring and calculating a concentration of effluent total phosphorus (TP) of wastewater in an aerobic tank, the system comprising: an influent tank; an anaerobic tank; an aerobic tank; a second setting tank; an effluent tank; and a plurality of sensors placed in the inlet tank, the anaerobic tank, the aerobic tank, the second setting tank, and the effluent tank to collect real-time information of variable parameters comprising a value of influent TP, a value of redox potential (ORP), a value of dissolved oxygen (DO), a temperature, a value of chemical oxygen demand (COD), a value of total nutrient (TN), and a value of total suspended solids (TSS).

In some embodiments, the plurality of sensors may include a molybdenum-blue colorimetric analyzer placed in the influent tank and configured to measure the value of influent TP, a ORP electrode sensor placed in the anaerobic tank as well as the effluent tank and configured to measure the value of ORP, a temperature sensor placed in the effluent tank and configured to measure the temperature, a pH sensor placed in the in the effluent tank and configured to measure the pH, a Teflon-coated-film based sensor placed in the aerobic tank and configured to measure the value of DO, a COD sensor placed in the effluent tank and configured to measure the value of COD, a TN sensor placed in the effluent tank and configured to measure the value of TN, a TSS sensor placed in the aerobic ad tank configured to measure the value of TSS.

For example, a TP sensor (e.g., WTW TresCon TP) may be configured to measure a centration of TP of the wastewater in influent tank. The measurement range is 0.01-3 mg/L, and the accuracy of the measurement is ±3%. The measurement interval is set to 30 minutes and the principle of measurement is molybdenum blue colorimetry. Further, a ORP sensor (e.g., WTW SensoLyt700IQ) may be configured to measure an ORP of the wastewater in anaerobic and effluent tank, and the measurement range is –2000-2000 mV. A DO sensor (e.g., WTW TriOxmatic700IQ) may be configured to measure a DO concentration of the wastewater in the aerobic tank, and the measurement range is 0-60 mg/L. The accuracy of the measurement is 0.01 mg/L. and the principle of measurement for the electrochemical method. A temperature sensor (WTW SensoLyt700IQ) may be configured to measure a temperature of the wastewater in effluent tank, and the measurement range is –5-60° C. A COD sensor (e.g., WTW CarboVis 705IQ) may be configured to measure a COD concentration in the in effluent tank, and the measurement range is 0.5-4000 mg/L. The accuracy of the measurement is 0.01 mg/L, and the principle of measurement for the electrochemical method, which may be used for measuring COD in influent, biological or effluent tank. A TN sensor (e.g., WTW TresCon A111+ON210+ON510) may be configured to measure a TN concentration in effluent tank, and the measurement range is 0-100 mg/L. The analyzer measures the concentrations of ammonia nitrogen, nitrate nitrogen and nitrite nitrogen by three modules, respectively, and the TN concentration is the sum of the three. A TSS sensor (e.g., WTW ViSolid700IQ) may be configured to measure a TSS concentration in aerobic tank, the measurement range is 0.003-1000 g/L, and the accuracy of the measurement is ±2%. A PH sensor (e.g., WTW SensoLyt700IQ) may be configured to measure a PH value of the wastewater in effluent tank and the measurement range is 0-100 mg/L.

In some embodiments, in the sewage treatment plant, the anaerobic tank, aerobic tank and secondary sedimentation tank are set up with different data sampling points, measuring the parameters of TP, ORP, DO, temperature, COD, TN, TSS and pH, respectively. When collecting, it is first necessary to mount the sensor electrode in a welded sleeve, which ensures that the sensor can be inserted into the deep enough water and fixed at the sampling point. Each sensor is equipped with a separate cable that stores the collected signals in a data logger via a cable. The data can be exported through the SD card or the USB interface, and the data can also be transmitted online by connecting the PLC device. The hardware system may include sensors, and PLC provides a large amount of real-time data. After the data is processed, it is used to select the auxiliary variables of the soft-sensing model and predict the total phosphorus of effluent.

Figure 19:
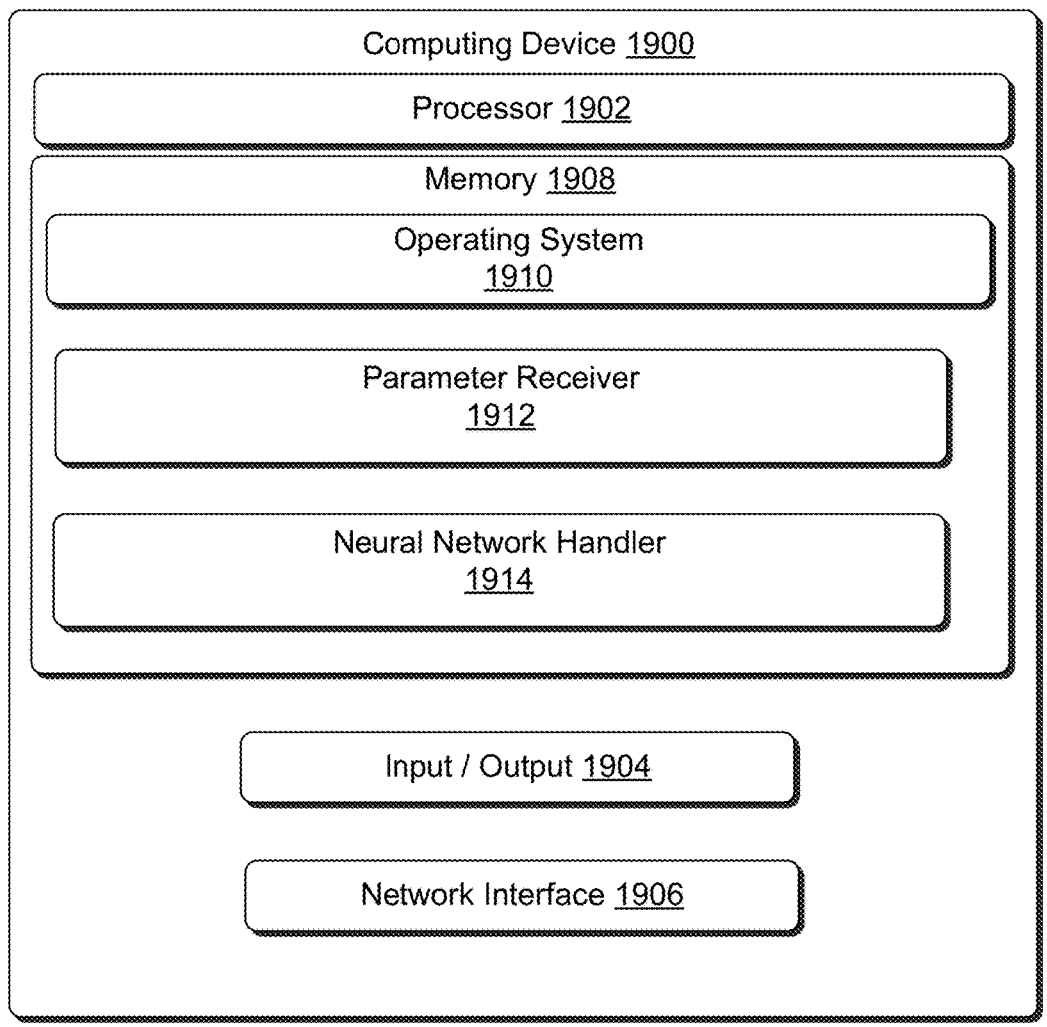
FIG. 19 is a schematic diagram of illustrative computing architectures of the computing device.

In some embodiments, the system may further include a computing device that may include one or more processors, and memory to maintain a plurality of components executable by the one or more processors. FIG. 19 is a schematic diagram of illustrative computing architectures of the computing device.

The computing device 1900 may be a user device or a server for a multiple location login control. In one exemplary configuration, the computing device 1900 includes one or more processors 1902, input/output interfaces 1904, network interface 1906, and memory 1908.

The memory 19508 may include computer-readable media in the form of volatile memory, such as random-access memory (RAM) and/or non-volatile memory, such as read only memory (ROM) or flash RAM. The memory 1908 is an example of computer-readable media.

Computer-readable media includes volatile and non-volatile, removable and non-removable media implemented in any method or technology for storage of information such as computer readable instructions, data structures, program modules, or other data. Examples of computer storage media include, but are not limited to, phase change memory (PRAM), static random-access memory (SRAM), dynamic random-access memory (DRAM), other types of random-access memory (RAM), read-only memory (ROM), electrically erasable programmable read-only memory (EEPROM), flash memory or other memory technology, compact disk read-only memory (CD-ROM), digital versatile disks (DVD) or other optical storage, magnetic cassettes, magnetic tape, magnetic disk storage or other magnetic storage devices, or any other non-transmission medium that may be used to store information for access by a computing device. As defined herein, computer-readable media does not include transitory media such as modulated data signals and carrier waves.

Turning to the memory 1908 in more detail, the memory 1908 may include an operating system 1910, a parameter receiver 1912 configured to receive the real-time information of variable parameters and a neural network handler 1914 configured to initialize a self-organizing radial basis function (SORBF) neural network, train the SORBF neural network using pre-measured training data consistent essentially of values of influent TP, values of redox potential, values of DO, temperatures, values of ORP, values of COD, values of TN, and values of TSS as well as corresponding values of effluent TP, and predict the value of effluent TP based on the received real-time information of variable parameters. Further detailed operations on the SORBF neural network are provided above in the present disclosure.

In some embodiments, the variable parameters consisting essentially of the value of influent TP, the value of ORP, the value of DO, the temperature, the value of COD, the value of TN, and the value of TSS. By "consisting essentially of" is meant including any elements listed after the phrase and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

In some embodiments, the variable parameters consisting of the value of influent TP, the value of ORP, the value of DO, the temperature, the value of COD, the value of TN, and the value of TSS.

In some embodiments, a measurement interval of the value of TP is about 30 minutes.

In some embodiments, the value of TN is a sum of values consisting of concentrations of ammonia nitrogen, nitrate nitrogen, and nitrite nitrogen.

In some embodiments, the training the SORBF neural network may include adjusting a network structure of the SORBF neural network, the network structure indicating a number of hidden neurons; adjusting neural network parameters of the SORBF neural network, the neural network parameters comprising a center value, a width, a connection weights of the network structure; and training the SORBF neural network using the adjusted neural network parameters.

Some embodiments relate to a system for measuring and calculating a value of effluent total phosphorus (TP) of a wastewater facility, which includes an influent tank, an anaerobic tank, an aerobic tank, a second setting tank, and an effluent tank. The system may include a molybdenum-blue colorimetric analyzer placed in an influent tank of the wastewater facility and configured to measure the value of influent TP, a ORP electrode sensor placed in the anaerobic tank as well as the effluent tank and configured to measure a value of ORP in the anaerobic tank and the effluent tank; a temperature sensor placed in the effluent tank and configured to measure a temperature in the effluent tank; a pH sensor placed in the in the effluent tank and configured to measure pH in the effluent tank; a Teflon-coated-film based sensor placed in the aerobic tank and configured to measure a value of DO in the aerobic tank; a COD sensor placed in the effluent tank and configured to measure a value of COD in the effluent tank; a TN sensor placed in the effluent tank and configured to a value of total nutrient (TN) in the effluent tank; a TSS sensor placed in the aerobic ad tank and configured to measure a value of TSS in the aerobic ad tank.

In some embodiments, the system may further include a computing device comprising: one or more processors, and memory to maintain a plurality of components executable by the one or more processors. The plurality of components may include a parameter receiver configured to receive real-time information of variable parameters consisting essentially of: the value of ORP in the anaerobic tank and the effluent tank, the temperature in the effluent tank, the pH of the effluent tank, the value of DO in the aerobic tank, the value of COD in the effluent tank, the value of TN in the effluent tank, and the value of TSS in the aerobic ad tank, a neural network handler configured to: initialize a SORBF neural network, train the SORBF neural network using pre-measured training data comprising the variable parameters, and predict, in a real-time manner, the value of effluent TP based on the received real-time information of variable parameters.

Conventional techniques implemented spectrophotometry, gas chromatography, liquid chromatography, and electrode-based methods to measure the value of effluent TP of a certain wastewater facility. However, some of parameters necessary for these techniques may require a long time (e.g., 30 mins to several hours) to be collected, rendering these techniques not available for real-time TP measurement and monitoring. The present disclosure selects several variable parameters, which may be timely and accurately measured and collected. Further, experimental data herein show that sensors suitable for measuring the variable parameters are placed in specific areas of the wastewater facility, respectively, to collect specific values of these variable parameters such that a SORBF neural network may be trained and predict, in a real-time manner, the value of effluent TP of the wastewater facility. For example, a molybdenum-blue colorimetric analyzer may be placed in the influent tank and configured to measure the value of influent TP, a ORP electrode sensor may be placed in the anaerobic tank as well as the effluent tank and configured to measure the value of ORP, a temperature sensor may be placed in the effluent tank and configured to measure the temperature, a pH sensor may be placed in the in the effluent tank and configured to measure the pH, a Teflon-coated-film based sensor may be placed in the aerobic tank and configured to measure the value of DO, a COD sensor may be placed in the effluent tank and configured to measure the value of COD, a TN sensor may be placed in the effluent tank and configured to measure the value of TN, and a TSS sensor may be placed in the aerobic ad tank configured to measure the value of TSS.

Some embodiments relate to a method for measuring and calculating a value of effluent TP of wastewater. The method may be implemented by the computing device 1900. In some embodiments, the processor 1902 may receive information that is collected by a plurality of sensors. For example, the information may include real-time information of variable parameters including a value of influent TP, a value of ORP, a value of DO, a temperature, a value of COD, a value of TN, and a value of TSS. The processor 1092 may further train a SORBF neural network using pre-measured training data consistent essentially of values of influent TP, values of redox potential, values of DO, temperatures, values of ORP, values of COD, values of TN, and values of TSS as well as corresponding values of effluent TP and predict the value of effluent TP using the trained SORBF neural network based on the received real-time information of variable parameters. Further detailed operations on the SORBF neural network are provided above in the present disclosure.

In some embodiments, the plurality of sensors may include a molybdenum-blue colorimetric analyzer placed in an influent tank and configured to measure the value of influent TP, a ORP electrode sensor placed in an anaerobic tank as well as the effluent tank and configured to measure the value of ORP, a temperature sensor placed in an effluent tank and configured to measure the temperature, a pH sensor placed in the in an effluent tank and configured to measure the pH, the value of ORP, and the temperature, a Teflon-coated-film based sensor placed in the aerobic tank and configured to measure the value of the DO, a COD sensor placed in the effluent tank and configured to measure the value of COD, a TN sensor placed in the effluent tank and configured to measure the value of TN, and a TSS sensor placed in the aerobic ad tank configured to measure the value of TSS.

In some embodiments, the variable parameters consisting essentially of the value of influent TP, the value of ORP, the value of DO, the temperature, the value of COD, the value of TN, and the value of TSS.

In some embodiments, the variable parameters consisting of the value of influent TP, the value of ORP, the value of DO, the temperature, the value of COD, the value of TN, and the value of TSS.

In some embodiments, a measurement interval of the value of TP is about 30 minutes.

In some embodiments, the value of TN is a sum of values consisting of concentrations of ammonia nitrogen, nitrate nitrogen, and nitrite nitrogen.

In some embodiments, the training the SORBF neural network may include adjusting a network structure of the SORBF neural network, the network structure indicating a number of hidden neurons, adjusting neural network parameters of the SORBF neural network, the neural network parameters comprising a center value, a width, a connection weights of the network structure, and training the SORBF neural network using the adjusted neural network parameters.

What is claimed is:

1. A system for monitoring a value of effluent total phosphorus (TP) of a wastewater facility, the system comprising:
    a molybdenum-blue colorimetric analyzer placed in an influent tank of the wastewater facility and configured to measure the value of influent TP, the wastewater facility comprising the influent tank, an anaerobic tank, an aerobic tank, a second setting tank, and an effluent tank;
    an ORP electrode sensor placed in the anaerobic tank as well as the effluent tank and configured to measure a value of redox potential (ORP) in the anaerobic tank and the effluent tank;
    a temperature sensor placed in the effluent tank and configured to measure a temperature in the effluent tank;
    a pH sensor placed in the in the effluent tank and configured to measure pH in the effluent tank;
    a Teflon-coated-film based sensor placed in the aerobic tank and configured to measure a value of dissolved oxygen (DO) in the aerobic tank;
    a COD sensor placed in the effluent tank and configured to measure a value of chemical oxygen demand (COD) in the effluent tank;
    a TN sensor placed in the effluent tank and configured to a value of total nutrient (TN) in the effluent tank;
    a TSS sensor placed in the aerobic ad tank and configured to measure a value of total suspended solids (TSS) in the aerobic ad tank; and
    a computing device comprising:
    one or more processors, and
    memory to maintain a plurality of components executable by the one or more processors, the plurality of components comprising:
    a parameter receiver configured to receive real-time information of variable parameters consisting essentially of:
    the value of ORP in the anaerobic tank and the effluent tank,
    the temperature in the effluent tank,
    the pH of the effluent tank,
    the value of DO in the aerobic tank,
    the value of COD in the effluent tank,
    the value of TN in the effluent tank, and
    the value of TSS in the aerobic ad tank,
    a neural network handler configured to:
    initialize a self-organizing radial basis function (SORBF) neural network,
    train the SORBF neural network based on pre-measured training data comprising the variable parameters, and
    predict, in a real-time manner, a value of current effluent TP based on the received real-time information of variable parameters.

2. The system of claim 1, wherein the variable parameters consisting of the value of influent TP, the value of ORP, the value of DO, the temperature, the value of COD, the value of TN, and the value of TSS.

3. The system of claim 1, wherein a measurement interval of the value of TP is about 30 minutes.

4. The system of claim 1, wherein the value of TN is a sum of values consisting of concentrations of ammonia nitrogen, nitrate nitrogen and nitrite nitrogen.

5. The system of claim 1, wherein the training the SORBF neural network comprises:
    adjusting a network structure of the SORBF neural network, the network structure indicating a number of hidden neurons;
    adjusting neural network parameters of the SORBF neural network, the neural network parameters comprising a center value, a width, a connection weights of the network structure; and
    training the SORBF neural network based upon the adjusted neural network parameters.

6. A method for monitoring a value of effluent TP of wastewater, the method comprising:
  measuring, by a plurality of sensors, real-time information of variable parameters comprising a value of influent TP, a value of ORP, a value of DO, a temperature, a value of COD, a value of TN, and a value of TSS;
  training, by the one or more processors, a SORBF neural network based upon pre-measured training data consistent essentially of values of influent TP, values of redox potential, values of DO, temperatures, values of ORP, values of COD, values of TN, and values of TSS as well as corresponding values of effluent TP; and
  predicting, by the one or more processors, a value of current effluent TP using the trained SORBF neural network based on the received real-time information of variable parameters.

7. The method of claim 6, wherein the training the SORBF neural network comprises:
  adjusting a network structure of the SORBF neural network, the network structure indicating a number of hidden neurons;
  adjusting neural network parameters of the SORBF neural network, the neural network parameters comprising a center value, a width, a connection weights of the network structure; and
  training the SORBF neural network based upon the adjusted neural network parameters.

8. The method of claim 6, wherein the plurality of sensors comprising:
  a molybdenum-blue colorimetric analyzer placed in an influent tank and configured to measure the value of influent TP,
  a ORP electrode sensor placed in an anaerobic tank as well as the effluent tank and configured to measure the value of ORP,
  a temperature sensor placed in an effluent tank and configured to measure the temperature,
  a pH sensor placed in the in an effluent tank and configured to measure the pH, the value of ORP, and the temperature,
  a Teflon-coated-film based sensor placed in the aerobic tank and configured to measure the value of the DO,
  a COD sensor placed in the effluent tank and configured to measure the value of COD,
  a TN sensor placed in the effluent tank and configured to measure the value of TN, and
  a TSS sensor placed in the aerobic ad tank configured to measure the value of TSS.

9. The method of claim 8, wherein the variable parameters consisting of the value of influent TP, the value of ORP, the value of DO, the temperature, the value of COD, the value of TN, and the value of TSS.

10. The method of claim 8, wherein a measurement interval of the value of TP is about 30 minutes.

11. The method of claim 8, wherein the value of TN is a sum of values consisting of concentrations of ammonia nitrogen, nitrate nitrogen and nitrite nitrogen.

12. The method of claim 6, wherein the training the SORBF neural network comprises:
  adjusting a network structure of the SORBF neural network, the network structure indicating a number of hidden neurons;
  adjusting neural network parameters of the SORBF neural network, the neural network parameters comprising a center value, a width, a connection weights of the network structure; and
  training the SORBF neural network based upon the adjusted neural network parameters.

13. The method of claim 6, wherein the plurality of sensors comprising:
  a molybdenum-blue colorimetric analyzer placed in an influent tank and configured to measure the value of influent TP,
  an ORP electrode sensor placed in an anaerobic tank as well as the effluent tank and configured to measure the value of ORP,
  a temperature sensor placed in an effluent tank and configured to measure the temperature,
  a pH sensor placed in the in an effluent tank and configured to measure the pH, the value of ORP, and the temperature,
  a Teflon-coated-film based sensor placed in the aerobic tank and configured to measure the value of the DO,
  a COD sensor placed in the effluent tank and configured to measure the value of COD,
  a TN sensor placed in the effluent tank and configured to measure the value of TN, and
  a TSS sensor placed in the aerobic ad tank configured to measure the value of TSS.

14. A method for monitoring a value of effluent TP of wastewater in a real-time manner, the method comprising:
  measuring, by a plurality of sensors, real-time information of variable parameters of a wastewater facility comprising an influent tank, an anaerobic tank, an aerobic tank, a second setting tank, and an effluent tank, the variable parameters comprising:
    a value of ORP in the anaerobic tank and the effluent tank,
    a temperature in the effluent tank,
    pH in the effluent tank,
    a value of DO in the aerobic tank,
    a value of COD in the effluent tank,
    a value of TN in the effluent tank, and
    a value of TSS in the aerobic ad tank; and
  training, by the one or more processors, a SORB neural network using pre-measured training data consistent of values of influent TP, values of redox potential, values of DO, temperatures, values of ORP, values of COD, values of TN, and values of TSS as well as corresponding values of effluent TP; and
  predicting, by the one or more processors, a value of current effluent TP based upon the trained SORBF neural network based on the received real-time information of variable parameters.

* * * * *